US008546336B2

(12) United States Patent
Chen et al.

(10) Patent No.: US 8,546,336 B2
(45) Date of Patent: Oct. 1, 2013

(54) SMAC PEPTIDOMETICS USEFUL AS IAP INHIBITORS

(75) Inventors: Zhuoliang Chen, Belmont, MA (US); Mark G. Charest, Cambridge, MA (US); Christine Hiu-Tung Chen, Waltham, MA (US); Miao Dai, Shanghai (CN); Feng He, Shanghai (CN); Huangshu Lei, Durham, NC (US); Ly Luu Pham, Arlington, MA (US); Sushil Kumar Sharma, West Orange, NJ (US); Christopher Sean Straub, Stow, MA (US); Run-Ming David Wang, Cambridge, MA (US); Fan Yang, West Roxbury, MA (US); Leigh Zawel, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/606,676

(22) Filed: Sep. 7, 2012
(Under 37 CFR 1.47)

(65) Prior Publication Data
US 2013/0005663 A1    Jan. 3, 2013

Related U.S. Application Data

(63) Continuation of application No. 12/376,057, filed as application No. PCT/US2007/074790 on Jul. 31, 2007.

(60) Provisional application No. 60/835,000, filed on Aug. 2, 2006.

(51) Int. Cl.
*A61K 38/00* (2006.01)

(52) U.S. Cl.
USPC ............... 514/19.3; 514/21.91; 546/279.1; 546/256; 548/236; 548/200; 548/181; 544/335; 544/329

(58) Field of Classification Search
USPC ............... 514/19.3, 21.91; 546/279.1, 256; 548/236, 200, 181; 544/335, 329
See application file for complete search history.

(56) References Cited

U.S. PATENT DOCUMENTS

| | | | |
|---|---|---|---|
| 4,278,793 A | 7/1981 | Durckheimer et al. |
| 4,551,273 A | 11/1985 | Tachibana et al. |
| 4,720,484 A | 1/1988 | Vincent et al. |
| 5,411,942 A | 5/1995 | Widmer et al. |
| 5,559,209 A | 9/1996 | Nishimoto |
| 6,472,172 B1 | 10/2002 | Deng et al. |
| 6,608,026 B1 | 8/2003 | Wang et al. |
| 7,067,274 B2 | 6/2006 | Fairbrother et al. |
| 7,419,975 B2 | 9/2008 | Palermo et al. |
| 7,718,600 B2 | 5/2010 | McLendon et al. |
| 2002/0160975 A1 | 10/2002 | Alnemri et al. |
| 2003/0157522 A1 | 8/2003 | Boudreault et al. |
| 2004/0171554 A1 | 9/2004 | Deshayes et al. |
| 2005/0197403 A1 | 9/2005 | Harran et al. |
| 2006/0128632 A1 | 6/2006 | Sharma et al. |
| 2006/0167066 A1 | 7/2006 | Cohen et al. |

FOREIGN PATENT DOCUMENTS

| | | |
|---|---|---|
| WO | 01/90070 A2 | 11/2001 |
| WO | WO 2005/069888 A2 | 8/2005 |
| WO | WO 2005/097791 A1 | 10/2005 |
| WO | 2006/014361 A1 | 2/2006 |
| WO | 2006/069063 A1 | 6/2006 |

OTHER PUBLICATIONS

Gordon, Tom et al. "Peptide Azoles: A New Class of Biologically-Active Dipeptide Mimetics", Bioorganic & Medicinal Chemistry Letters, 1993, vol. 3, No. 5, pp. 915-920, Pergamon Press Ltd., Great Britain.
Liu, Zhihong et al. "Structural Basis for Binding of Smac/DIABLO to the XIAP BIR3 Domain", Nature, 2000, vol. 408, pp. 1004-1008.
Thompson, Scott K. et al. "Synthesis and Antiviral Activity of a Novel Class of HIV-1 Protease Inhibitors Containing a Heterocyclic P1'-P2' Amide Bond Isostere", Bioorganic & Medicinal Chemistry Letters, 1994, vol. 4, No. 20, pp. 2441-2446, Elsevier Science Ltd., Great Britain.
Thompson, Scott K. et al. "Rational Design, Synthesis, and Crystallographic Analysis of a Hydroxyethylene-Based HIV-1 Protease Inhibitor Containing a Heterocyclic P1'-P2' Amide Bond Isostere", J. Med. Chem., 1994, vol. 37, pp. 3100-3107.
Thompson, Scott K. et al. "Design of Potent and Selective Human Cathepsin K Inhibitors that Span the Active Site", Proc. Natl. Acad. Sci. USA, Dec. 1997, vol. 94, pp. 14249-14254.
Wu, Geng et al. "Structural Basis of IAP Recognition by Smac/Diablo", Nature, 2000, vol. 408, pp. 1008-1012.
Lawton et al., "A Bioactive Modified Peptide, Aeruginosamide, Isolated from the Cyanobacterium *Microcystis aeruginosa*" The Journal of Organic Chemistry, 1999 vol. 64 pp. 5329-5332.
Stables et al., "A Novel Peptidic Tachykinin Antagonist Which is Potent at NK3 Receptors", Neuropeptides, 1994 vol. 27 pp. 333-341.

(Continued)

*Primary Examiner* — Jeffrey S. Lundgren
*Assistant Examiner* — Ibrahim D Bori
(74) *Attorney, Agent, or Firm* — Arlene K. Musser

(57) ABSTRACT

The present invention is directed to a compound of the formula:

or pharmaceutically acceptable salts thereof and use of such compounds for treating proliferative diseases such as cancer, in mammals.

3 Claims, No Drawings

(56) References Cited

OTHER PUBLICATIONS

Arnt et al., "Synthetic SMAC/Diablo peptides enhance the effects of chemotherapeutic agents by binding XIAP and CIAP1 in situ", Journal of Biological Chemistry, vol. 277 (46), pp. 44236-44243, (2002).

Kipp et al., "Molecular targeting of inhibitor of apoptosis based on small molecule mimics of natural binding partners", Biochemistry, vol. 41 (23), pp. 7344-7349, (2002).

Wu et al., "Structural analysis of a functional DJAP1 fragment bound to grim and hid peptides", Molecular Cell, vol. 8 (1), pp. 95-104, (2001).

Deal et al., "Conformationally constrained tachykinin analogues: potent and highly selective neurokinin NK-2-receptor antagonists", Journal of Medicinal Chemistry, vol. 35 (22), pp. 4195-4204, (1992).

Deng et al., "Kinetic Control of Proline Amide Rotamers: Total Synthesis of trans,trans and cis,cis-Ceratospongamide", J. Am. Chem. Soc., 2002 vol. 124 No. 6 pp. 916-917.

Klein et al., "Lyngbyapeptin A, a modified tetrapeptide from *Lyngbya bouillonii* (Cyanophyceae)", Tetrahedron Letters, 1999 vol. 40 pp. 695-696.

Pichon-Pesme et al., "On Building a Data Bank of Transferable Experimental Electron Density Parameters: Application to Polypeptides", J. Phys. Chem., 1995 vol. 99 pp. 6242-6250.

Yokokawa et al., "Total Synthesis of cis,cis-Ceratospongamide, a Bioactive Thiazole-Containing Cyclic Peptide from Marine Origin", Synlett, 2001 Special Issue pp. 986-988.

Yokokawa et al., "Total synthesis and conformational studies of ceratospongamide, a bioactive cyclic heptapeptide from marine origin", Tetrahedron, 2002 vol. 58 pp. 8127-8143.

Patani George A. et al., "Bioisosterism: A Rational Approach in Drug Design", Chem. Rev., 1996, 96, 3147-3176.

Office Communication sent electronically on Jan. 19, 2012 for U.S. Appl. No. 13/178,946.

Li et al., "A Small Molecule Smac Mimic Potentiates TRAIL- and TNFa-Mediated Cell Death", Science, 2004 vol. 305 pp. 1471-1474.

SMAC PEPTIDOMETICS USEFUL AS IAP INHIBITORS

The present invention relates generally to novel compounds that inhibit the binding of the Smac protein to Inhibitor of Apoptosis Proteins (IAPs). More specifically, the present invention includes novel compounds, novel compositions, methods of their use and methods of their manufacture, where such compounds are generally pharmacologically useful as agents in therapies whose mechanism of action rely on the inhibition of the Smac/IAP interaction, and more particularly useful in therapies for the treatment of proliferative diseases, including cancer.

BACKGROUND

Programmed cell death plays a critical role in regulating cell number and in eliminating stressed or damaged cells from normal tissues. Indeed, the network of apoptotic signaling mechanisms inherent in most cell types provides a major barrier to the development and progression of human cancer. Since most commonly used radiation and chemo-therapies rely on activation of apoptotic pathways to kill cancer cells, tumor cells which are capable of evading programmed cell death often become resistant to treatment.

Apoptosis signaling networks are classified as either intrinsic when mediated by death receptor-ligand interactions or extrinsic when mediated by cellular stress and mitochondrial permeabilization. Both pathways ultimately converge on individual Caspases. Once activated, Caspases cleave a number of cell death-related substrates, effecting destruction of the cell.

Tumor cells have devised a number of strategies to circumvent apoptosis. One recently reported molecular mechanism involves the overexpression of members of the IAP family. IAPs sabotage apoptosis by directly interacting with and neutralizing Caspases. The prototype IAPs, XIAP and cIAP have three functional domains referred to as BIR 1, 2 & 3 domains. BIR3 domain interacts directly with Caspase 9 and inhibits its ability to bind and cleave its natural substrate, Procaspase 3.

It has been reported that a proapoptotic mitochondrial protein, Smac (also known as DIABLO), is capable of neutralizing XIAP and/or cIAP by binding to a peptide binding pocket (Smac binding site) on the surface of BIR3 thereby precluding interaction between XIAP and/or cIAP and Caspase 9. The present invention relates to therapeutic molecules that bind to the Smac binding pocket thereby promoting apoptosis in rapidly dividing cells. Such therapeutic molecules are useful for the treatment of proliferative diseases, including cancer.

SUMMARY OF THE INVENTION

The present invention relates to novel compounds of formula (I):

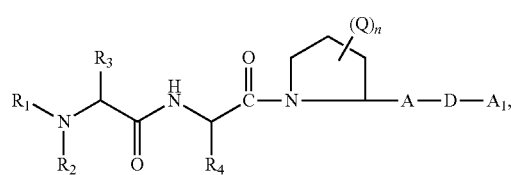

or pharmaceutically acceptable salts thereof, wherein
$R_1$ is H, $C_1$-$C_4$ alkyl, $C_2$-$C_4$ alkenyl, $C_2$-$C_4$ alkynyl or $C_3$-$C_{10}$ cycloalkyl, which $R_1$ may be unsubstituted or substituted;

$R_2$ is H, $C_1$-$C_4$ alkyl, $C_2$-$C_4$ alkenyl, $C_2$-$C_4$ alkynyl, $C_3$-$C_{10}$ cycloalkyl which $R_2$ may be unsubstituted or substituted;

$R_3$ is H, $CF_3$, $C_2F_5$, $C_1$-$C_4$ alkyl, $C_2$-$C_4$ alkenyl, $C_2$-$C_4$ alkynyl, $CH_2$—Z, or $R_2$ and $R_3$, taken together with the nitrogen atom to which they are attached, form a heterocyclic ring, which alkyl, alkenyl, alkynyl or het ring may be unsubstituted or substituted;

Z is H, OH, F, Cl, $CH_3$, $CH_2Cl$, $CH_2F$ or $CH_2OH$;

$R_4$ is $C_{0-10}$ alkyl, $C_{0-10}$ alkenyl, $C_0$-$C_{10}$ alkynyl, $C_3$-$C_{10}$ cycloalkyl, wherein the $C_{0-10}$ alkyl, or cycloalkyl group is unsubstituted or substituted;

A is het, which may be substituted or unsubstituted;

D is $C_1$-$C_7$ alkylene or $C_2$-$C_9$ alkenylene, C(O), O, $NR_7$, S(O)r, C(O)—$C_1$-$C_{10}$ alkyl, O—$C_1$-$C_{10}$ alkyl, S(O)r-$C_1$-$C_{10}$ alkyl, C(O)$C_0$-$C_{10}$ arylalkyl, O$C_0$-$C_{10}$ arylalkyl, or S(O)r $C_0$-$C_{10}$ arylalkyl, which alkyl and aryl groups may be unsubstituted or substituted;

r is 0, 1 or 2;

$A_1$ is a substituted or unsubstituted aryl or unsubstituted or substituted het which substituents on aryl and het are halo, alkyl, lower alkoxy, $NR_5R_6$, CN, $NO_2$ or $SR_5$;

each Q is independently H, $C_1$-$C_{10}$ alkyl, $C_1$-$C_{10}$ alkoxy, aryl $C_1$-$C_{10}$ alkoxy, OH, O—$C_1$-$C_{10}$ alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$ het, het, O—$(CH_2)_{1-6}$ het, $C(O)R_{11}$, —$C(O)N(R_{11})(R_{12})$, $N(R_{11})(R_{12})$, $SR_{11}$, $S(O)R_{11}$, $S(O)_2R_{11}$, $S(O)_2$—$N(R_{11})(R_{12})$, or $NR_{11}$—$S(O)_2$—$(R_{12})$, wherein alkyl, cycloalkyl and aryl are unsubstituted or substituted;

n is 0, 1, 2 or 3, 4, 5, 6 or 7;

het is a 5- to 7-membered monocyclic heterocyclic ring containing 1-4 heteroring atoms selected from N, O and S or an 8- to 12-membered fused ring system that includes one 5- to 7-membered monocyclic heterocyclic ring containing 1, 2 or 3 heteroring atoms selected from N, O and S, which het is unsubstituted or substituted;

$R_{11}$ and $R_{12}$ are independently H, $C_1$-$C_{10}$ alkyl, $(CH_2)_{0-6}$—$C_3$-$C_7$ cycloalkyl, $(CH_2)_{0-6}$—$(CH)_{0-1}$ $(aryl)_{1-2}$, $C(O)$—$C_1$-$C_{10}$ alkyl, —$C(O)$—$(CH_2)_{1-6}$—$C_3$-$C_7$ cycloalkyl, —$C(O)$—O—$(CH_2)_{0-6}$-aryl, —$C(O)$—$(CH_2)_{0-6}$—O-fluorenyl, $C(O)$—NH—$(CH_2)_{0-6}$-aryl, $C(O)$—$(CH_2)_{0-6}$-aryl, $C(O)$—$(CH_2)_{1-6}$-het, —$C(S)$—$C_1$-$C_{10}$alkyl, —$C(S)$—$(CH_2)_{1-6}$—$C_3$-$C_7$cycloalkyl, —$C(S)$—O—$(CH_2)_{0-6}$-aryl, —$C(S)$—$(CH_2)_{0-6}$—O-fluorenyl, $C(S)$—NH—$(CH_2)_{0-6}$-aryl, —$C(S)$—$(CH_2)_{0-6}$-aryl or $C(S)$—$(CH_2)_{1-6}$-het, $C(O)R_{11}$, $C(O)NR_{11}R_{12}$, $C(O)OR_{11}$, $S(O)nR_{11}$, $S(O)_mNR_{11}R_{12}$, m=1 or 2, $C(S)R_{11}$, $C(S)NR_{11}R_{12}$, $C(S)OR_{11}$, wherein alkyl, cycloalkyl and aryl are unsubstituted or substituted; or $R_{11}$ and $R_{12}$ are a substituent that facilitates transport of the molecule across a cell membrane, or $R_{11}$ and $R_{12}$ together with the nitrogen atom form het, wherein
the alkyl substituents of $R_{11}$ and $R_{12}$ may be unsubstituted or substituted by one or more substituents selected from $C_1$-$C_{10}$ alkyl, halogen, OH, O—$C_1$-$C_6$ alkyl, —S—$C_1$-$C_6$ alkyl, $CF_3$ or $NR_{11}R_{12}$,
substituted cycloalkyl substituents of $R_{11}$ and $R_{12}$ are substituted by one or more substituents selected from a $C_2$-$C_{10}$ alkene; $C_1$-$C_6$ alkyl; halogen; OH; O—$C_1$-$C_6$ alkyl; S—$C_1$-$C_6$ alkyl, $CF_3$; or $NR_{11}R_{12}$ and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CNO—C(O)—$C_1$-$C_4$alkyl and C(O)—O—$C_1$-$C_4$-alkyl;

$R_5$, $R_6$ and $R_7$ are independently hydrogen, lower alkyl, aryl, aryl lower alkyl, cycloalkyl, or cycloalkyl lower alkyl, $C(O)R_5$; $S(O)R_5$, $C(O)OR_5$, $C(O)NR_5R_6$, and the substituents on $R_1$, $R_2$, $R_3$, $R_4$, Q, and A and $A_1$ groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P(=O)(OH)$_2$), hydroxy-lower alkoxy phosphoryl or di-lower alkoxyphosphoryl, $(R_9)NC(O)$—$NR_{10}R_{13}$, lower alkyl carbamic acid ester or carbamates or —$NR_8R_{14}$, wherein $R_8$ and $R_{14}$ can be the same or different and are independently H or lower alkyl, or $R_8$ and $R_{14}$, together with the N atom, form a 3- to 8-membered heterocyclic ring containing a nitrogen heteroring atoms and may optionally contain one or two additional heteroring atoms selected from nitrogen, oxygen and sulfur, which heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio; and $R_9$, $R_{10}$ and $R_{13}$ are independently hydrogen, lower alkyl, halogen substituted lower alkyl, aryl, aryl lower alkyl, halogen substituted aryl, halogen substituted aryl lower alkyl.

The present invention also relates to pharmaceutical compositions comprising therapeutically effective amounts of compounds of formula (I), as defined hereinabove, or a pharmaceutically acceptable salt thereof, and a pharmaceutical carrier therefor. In another embodiment, the present invention is directed to a method of treating a mammal, especially human, afflicted with a proliferative disease, especially those dependent on the binding of the smac protein to IAPs, such as cancer, which method comprises administering to said mammal in need of treatment an anti-proloferative effective amount of a compound of formula (I), or a pharmaceutically acceptable salt thereof. The present invention is also directed to the manufacture of compounds of formula (I), for use in the treatment of said diseases.

DETAILED DESCRIPTION OF THE PRESENT INVENTION

As used herein, the term "aryl" is defined as an aromatic radical having 6-14 ring carbon atoms, and no ring heteroatoms. The aryl group may be monocyclic or fused bicyclic or tricyclic. It may be unsubstituted or substituted by one or more, preferably one or two, substituents, wherein the substituents are as described herein. As defined herein, the aryl moiety may be completely aromatic regardless of whether it is monocyclic or bicyclic. However, if it contains more than one ring, as defined herein, the term aryl includes moieties wherein at least one ring is completely aromatic while the other ring(s) may be partially unsaturated or saturated or completely aromatic. Preferred "aryl" is phenyl, naphthyl or indanyl. The most preferred aryl is phenyl.

"Het", as used herein, refers to heteroaryl and heterocyclic compounds containing at least one S, O or N ring heteroatom. More specifically, "het" is a 5- to 7-membered heterocyclic ring containing 1-4 heteroatoms selected from N, O and S, or an 8- to 12-membered fused ring system including at least one 5- to 7-membered heterocyclic ring containing 1, 2 or 3 heteroatoms selected from N, O and S. Examples of het, as used herein, include unsubstituted and substituted pyrrolidyl, tetrahydrofuryl, tetrahydrothiofuryl, piperidyl, piperazyl, purinyl, tetrahydropyranyl, morpholino, 1,3-diazapanyl, 1,4-diazapanyl, 1,4-oxazepanyl, 1,4-oxathiapanyl, furyl, thienyl, pyrryl, pyrrolyl, pyrazolyl, triazolyl, tetrazolyl, indazolyl, oxadiazolyl, imidazolyl, pyrrolidyl, pyrrolidinyl, thiazolyl, oxazolyl, pyridyl, pyrazolyl, pyrazinyl, pyrimidinyl, isoxazolyl, pyrazinyl, quinolyl, isoquinolyl, pyridopyrazinyl, pyrrolopyridyl, furopyridyl, indolyl, benzofuryl, benzothiofuryl, benzoindolyl, benzothienyl, pyrazolyl, piperidyl, piperazinyl, indolinyl, morpholinyl, benzoxazolyl, pyrroloquinolyl, and the like. Heteroaryls are within the scope of the definition of het. Examples of heteroaryls are pyridyl, pyrimidinyl, quinolyl, thiazolyl and benzothiazolyl. The most preferred het are pyridyl, pyrimidinyl and thiazolyl. The het may be unsubstituted or substituted as described herein. It is preferred that it is unsubstituted or if substituted it is substituted on a carbon atom by halogen, especially fluorine or chlorine, hydroxy, $C_1$-$C_4$ alkyl, such as methyl and ethyl, $C_1$-$C_4$ alkoxy, especially methoxy and ethoxy, nitro, —O—C(O)—$C_1$-$C_4$ alkyl or —C(O)—O—$C_1$-$C_4$ alkyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, sulfonate, sulfanyl, SCN or nitro or on a nitrogen atom by $C_1$-$C_4$ alkyl, especially methyl or ethyl, —O—C(O)—$C_1$-$C_4$ alkyl or —C(O)—O—$C_1$-$C_4$ alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazole, and the like, wherein such het may be unsubstituted or substituted as defined hereinabove.

Halogen is fluorine, chlorine, bromine or iodine, especially fluorine and chlorine.

Unless otherwise specified, "alkyl", either above or in combination, includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

A "cycloalkyl" group means $C_3$-$C_{10}$ cycloalkyl having 3-10 ring carbon atoms and may be, e.g., cyclopropyl, cyclobutyl, cyclopentyl, cyclohexyl, cycloheptyl or cyclooctyl, cyclononyl and the like. The cycloalkyl group may be monocyclic or fused bicyclic. It is preferred that it is monocyclic. Moreover, the preferred cycloalkyl group is cyclopentyl or cyclohexyl. Most preferably, cycloalkyl is cyclohexyl.

The cycloalkyl group may be fully saturated or partially unsaturated, although it is preferred that it is fully saturated. As defined herein, it excludes aryl groups. The cycloalkyl groups may be unsubstituted or substituted with any of the substituents defined below, preferably halo, hydroxy or $C_1$-$C_6$ alkyl, such as methyl.

Substituents that facilitate transport of the molecule across a cell membrane are known to those of skill in the medicinal chemistry arts [see, e.g., Gangewar S. et al., *Drug Discov Today*, Vol. 2, pp. 148-155 (1997); and Bundgaard H. and Moss *J., Pharma Res*, Vol. 7, p. 885 (1990)]. Generally, such substituents are lipophillic substituents. Such lipophillic substituents include a $C_6$-$C_{30}$ alkyl which is saturated, monounsaturated, polyunsaturated, including methylene-interrupted polyene, phenyl, phenyl which is substituted by one or two $C_1$-$C_8$ alkyl groups, $C_5$-$C_9$ cycloalkyl, $C_5$-$C_9$ cycloalkyl which is substituted by one or two $C_1$-$C_8$ alkyl groups, —$X_1$-phenyl, —$X_1$-phenyl which is substituted in the phenyl ring by one or two $C_1$-$C_8$ alkyl groups, $X_1$—$C_5$-$C_9$ cycloalkyl or $X_1$—$C_5$-$C_9$ cycloalkyl which is substituted by one or two $C_1$-$C_8$ alkyl groups; where $X_1$ is $C_1$-$C_{24}$ alkyl which is saturated, monounsaturated or polyunsaturated and straight or branched chain.

Unsubstituted is intended to mean that hydrogen is the only substituent.

Except as described herein, any of the above defined aryl, het, alkyl, alkenyl, alkynyl or cycloalkyl, may be unsubstituted or independently substituted by up to four, preferably one, two or three substituents, selected from the group consisting of: halo, such as Cl or Br; hydroxy; lower alkyl, such as $C_1$-$C_3$ alkyl; lower alkyl which may be substituted with any of the substituents defined herein; lower alkenyl; lower alkynyl; lower alkanoyl; lower alkoxy, such as methoxy; aryl, such as phenyl or naphthyl; substituted aryl, such as fluoro phenyl or methoxy phenyl; aryl lower alkyl, such as benzyl, amino, mono or di-lower alkyl, such as dimethylamino; lower alkanoyl amino acetylamino; amino lower alkoxy, such as ethoxyamine; nitro; cyano; cyano lower alkyl; carboxy; lower carbalkoxy, such as methoxy carbonyl; n-propoxy carbonyl or iso-propoxy carbonyl, lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl, such as methyl sulfanyl; sulfoamino; aryl sulfonamide; halogen substituted or unsubstituted aryl sulfonate, such as chloro-phenyl sulfonate; lower alkylsulfinyl; arylsulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane alkoxyphosphoryl; urea and substituted urea of the formula $(R_9)$ NC(O) N($R_{10}$), ($R_{13}$), wherein $R_9$, $R_{10}$ and $R_{13}$ are as defined herein, such as urea or 3-trifluoro-methyl-phenyl urea; alkyl carbamic acid ester or carbamates, such as ethyl-N-phenyl-carbamate; or —$NR_8R_{14}$, wherein $R_8$ and $R_{14}$ can be the same or different and are independently H; lower alkyl, e.g., methyl, ethyl or propyl; or $R_8$ and $R_{14}$, together with the N atom, form a 3- to 8-membered heterocyclic ring containing a nitrogen heteroring atom and optionally one or two additional heteroring atoms selected from the group consisting of nitrogen, oxygen and sulfur (e.g. piperazinyl, pyrazinyl, lower alkyl-piperazinyl, pyridyl, indolyl, thiophenyl, thiazolyl, benzothiophenyl, pyrrolidinyl, piperidino or imidazolinyl) where the heterocyclic ring may be substituted with any of the substituents defined hereinabove.

Preferably the above mentioned alkyl, cycloalkyl, and aryl groups are independently unsubstituted or are substituted by lower alkyl, aryl, aryl lower alkyl, carboxy, lower carbalkoxy and especially halogen, —OH, —SH, —$OCH_3$, —$SCH_3$, —CN, —SCN or nitro.

As defined herein, the term "lower alkyl", when used alone or in combination, refers to alkyl containing 1-6 carbon atoms. The alkyl group may be branched or straight-chained, and is as defined hereinabove.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include ethenyl, 1-propenyl, 2-propenyl, 1-butenyl, 2-butenyl, 2-methyl-1-propenyl, 1,3-butadienyl and the like. The preferred alkenyl group is ethenyl.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. It is preferred that the alkynyl group contains 1 or 2 carbon-carbon triple bonds and more preferably one carbon-carbon triple bond. The alkynyl group may be straight chained or branched. Examples include ethynyl, 1-propynyl, 2-propynyl, 1-butynyl, 2-butynyl and the like. The preferred alkynyl group is ethynyl.

As used herein, the term "aryl alkyl" refers to a aryl group connected to the main chain by a bridging alkylene group. Examples include benzyl, phenethyl, naphthylmethyl, and the like. The preferred aryl alkyl is benzyl. Similarly, cyano alkyl group refers to a cyano group connected to the main chain by a bridging alkylene group.

The term "alkyl aryl" on the other hand, refers to an alkyl group bridged to the main chain through a phenylene group. Examples include methylphenyl, ethylphenyl and the like.

As used herein, the term "lower alkanoyl" refers to a lower alkyl chain in which one of the carbon atoms is replaced by a C=O group. The C=O group may be present at one of the ends of the substituent or in the middle of the moiety. Examples include formyl, acetyl, 2-propanoyl, 1-propanoyl and the like.

The term "alkoxy" refers to an alkyl group as defined herein, connected to the main chain by an oxygen atom. Examples include methoxy, ethoxy and the like.

The term "lower thioalkyl" refers to an alkyl group, as defined herein, connected to the main chain by a sulfur atom. Examples include thiomethyl (or mercapto methyl), thioethyl (mercapto ethyl) and the like.

The term "lower carbalkoxy" or synonym thereto refers to an alkoxycarbonyl group, where the attachment to the main chain is through the aryl group (C(O)). Examples include methoxy carbonyl, ethoxy carbonyl and the like.

It is to be understood that the terminology C(O) refers to a —C=O group, whether it be ketone, aldehyde or acid or acid derivative. Similarly, S(O) refers to a —S=O group.

As used herein, the term S(O)r refers to the number of oxygen atoms bonded to the sulfur atom. When r=2, then S(O)r=$SO_2$, when r is 1, then S(O)r is SO; and when r=O, then S(O)r is S.

The term "$C_o$", as used herein, as part of a definition of alkyl as, e.g., $C_{0-10}$, refers to zero carbon atoms. Thus, "$C_0$-$C_{10}$ aryl alkyl" means that the aryl group is bonded directly to the main chain ($C_o$) or that there is a $C_1$-$C_{10}$ alkylene group bridging the main chain to an aryl group.

The term "$(CH_2)_{0-6}$" as part of definition of a larger group, e.g., $(CH_2)_{0-6}$ $C_3$-$C_7$ cycloalkyl, refers to a group that is not present $(CH_2)_0$, or to a group that contains 1-6 carbon atoms $(CH_2)_{1-6}$.

The term "$(CH_2)_{0-6}$—$(CH)_{0-1}$, $(aryl)_{1-2}$", in the definition of $R_{11}$ and $R_{12}$, is intended to mean one of the following $(CH_2)_{1-6}$-aryl, aryl, —CH(aryl)$_2$ or $(CH_2)_{1-6}$ (CH) (aryl)$_2$.

As used herein, the variable "n" refers to number of substitutents on the pyrrolidinyl (tetrahydropyrrolyl) ring. The term "n" is defined as 0-7 and it determines the number of Q substituents on the pyrrolidinyl (tetrahydro-pyrrolyl) ring. Q can only be present at the 2, 3, 4 or 5 positions of the pyrrolidinyl ring, i.e., at the carbon atoms of the pyrrolidinyl ring. Except for carbon number 2 that can allow for one substitution, each of other carbon atoms are saturated and each of them may have two substituents thereon. When n is 7, then each of the carbon atoms are bonded with Q as defined herein. Each Q may be the same or different. However, when n is 6, then one of the seven possible substituents is H, and the other five are Q, which can be the same or different. Further, when n is 5, then two of the possible substitutents are H, and the other five are independently Q, as defined herein. When n is 4, then three of the seven possible substituents are H, and the remainder are Q independently as defined herein. Where n is 3, then four of the seven possible substituents are H, and the other three are Q as defined herein. When n is 2, then two of the seven possible substituent are Q, and the remainder are H. When n is 1, then only one of the seven possible substituent is Q, and the remainder are H. Finally, when n is 0, all seven of the substituents are H.

It is to be understood that each of the Q substituents may be the same or they may be different.

Where the plural form is used for compounds, salts, pharmaceutical preparations, this is intended to mean also a single compound, single pharmaceutical preparation, salt and the like.

It will be apparent to one of skill in the art that the compounds of the present invention can exist as a salt form, especially as an acid addition salt or a base addition salt. When a compound exists in a salt form, such salt forms are included within the scope of the invention. Although any salt form may be useful in chemical manipulations, such as purification procedures, only pharmaceutically acceptable salts are useful for the pharmaceutical products of the present invention.

Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts and the like. Acid addition salts include inorganic acid addition salts, such as hydrochloride, sulfate and phosphate; and organic acid addition salts, such as alkyl sulfonate, arylsulfonate, acetate, maleate, fumarate, tartrate, citrate and lactate and the like. Examples of metal salts are alkali metal salts, such as lithium salt, sodium salt and potassium salt; alkaline earth metal salts, such as magnesium salt and calcium salt, aluminum salt, and zinc salt and the like. Examples of ammonium salts are ammonium salts and tetramethylammonium salts and the like. Examples of organic amine addition salts are salts with morpholine and piperidine and the like. Examples of amino acid addition salts are salts with glycine, phenylalanine, glutamic acid and lysine and the like. Sulfonate salts include mesylate, tosylate and benzene sulfonic acid salts and the like.

In view of the close relationship between the compounds in free form and those in the form of their salts, including those salts that can be used as intermediates, e.g., in the purification or identification of the compounds, tautomers or tautomeric mixtures and their salts, any reference to the compounds hereinbefore and hereinafter especially the compounds of the formulae (I)-(VII), is to be understood as referring also to the corresponding tautomers of these compounds, especially of compounds of the formulae (I)-(VII), tautomeric mixtures of these compounds, especially of compounds of the formulae (I)-(VII), or salts of any of these, as appropriate and expedient and if not mentioned otherwise.

Any asymmetric carbon atom may be present in the (R)—, (S)— or (R,S)-configuration, preferably in the (R)- or (S)-configuration. Substituents at a ring at atoms with saturated bonds or substituents on carbon-carbon double bonds may, if possible, be present in cis-(=Z—) or trans (=E-) form. The compounds may thus be present as mixtures of isomers or preferably as pure isomers, preferably as enantiomermally pure diastereomers or pure enantiomers.

The present invention includes within its scope, prodrugs of the compounds of the invention. In general, such prodrugs will be functional derivatives of a compound of the invention which are readily convertible in vivo into the compound from which it is notionally derived. Conventional procedures for the selection and preparation of suitable prodrugs are described, e.g., in *Design of Prodrugs*, H. Bundgaard, Ed., Elsevier (1985).

The preferred $R_1$ group is H and $C_1$-$C_4$ alkyl especially methyl. $R_1$ may be unsubstituted or substituted and is most preferably unsubstituted. The most preferred values of $R_1$ is H, methyl and ethyl, and especially methyl or ethyl and most especially methyl.

$R_2$ is preferably H or $C_1$-$C_4$ alkyl, especially methyl. $R_2$ may be unsubstituted or substituted. It is most preferably unsubstituted. It is preferred that $R_2$ is hydrogen.

$R_3$ is preferably H or $C_1$-$C_4$ alkyl especially hydrogen methyl, or ethyl and most especially methyl or ethyl, and most especially methyl, which may be unsubstituted or substituted. $R_3$ may be unsubstituted or substituted as defined herein. It is preferred that it is unsubstituted methyl.

$R_4$ is preferably $C_5$-$C_7$ cycloalkyl, and more preferably cyclopentyl or cyclohexyl, isproyl, and most preferably is cyclohexyl. One may be substituted or unsubstituted. If substituted, it is preferably substituted with lower alkyl especially methyl. However, it is preferred that $R_4$ is unsubstituted.

The pyrrolidinyl ring can have up to six independent Q substituents thereon. It is preferred that n is 0-3 and even more preferably, n is 0, 1, or 2 and even more preferably, n is 0 or 1 and most preferably n is 0. If Q is present, it is preferred that Q is lower alkyl, alkoxyl, alylthio, amino, sulfonylamino, acylamino.

A is preferably a 5- or 6-membered het, and more preferably is 5- or 6-membered heteroaryl, especially a 5 or 6-member heteroaryl ring containing at least one ring hetero atom selected from the group consisting of nitrogen, oxygen and sulfur and containing 1-4 ring heteroatoms. Preferably, it contains 1 or 2 ring heteroatoms, and more preferably contains at least 1 N ring heteroatom, and the other ring heteroatom is, if present, a nitrogen, oxygen or sulfur, and more preferably if present is nitrogen or sulfur, and most preferably, if present, is sulfur. The preferred value of A is pyridyl, pyrimidinyl, and thiazolyl. A may be unsubstituted or substituted. It is preferred that A is unsubstituted or substituted with alkyl, amino or halo.

D is preferably O or C(O), NR, or S(O)r and more preferably is O or C(O), CH₃N, HN or S and even more preferably is O or C(O) or CH₃N, HN and most preferably O or C(O).

A₁ is preferably a substituted aryl or an unsubstituted or substituted 5- or 6-membered het and more preferably is a substituted aryl or a 5- or 6-membered unsubstituted or substituted heteroaryl. Most preferably, A₁ is a substituted aryl. The most preferred value of A₁ is a substituted phenyl.

It is preferred that if A is aryl, it is monosubstituted, disubstituted or trisubstituted by one of the substituents enumerated hereinabove. In an embodiment, A₁ is substituted by halo, especially fluoro or chloro, and most preferably fluoro.

Another embodiment of the compound of formula (I) has formula (II):

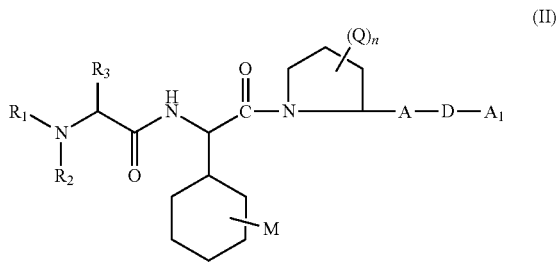

or pharmaceutically acceptable salts thereof, wherein
wherein
R₁, R₂, R₃, Q, n, A, D and A₁ are as described hereinabove; and
M is a H or a substituent on the cyclohexyl group, as defined above.

It is preferred that M is H, halo; hydroxy; lower alkyl; lower alkenyl; lower alkynyl; formyl; lower alkanoyl; aryl, cycloalkyl, aryl lower alkyl, lower alkoxy; aryl lower alkyl, amino; amino, mono- or disubstituted lower alkylamino; amino lower alkyl; lower alkanoyl; amino lower alkoxy; nitro; cyano; cyano lower alkyl; carboxy; lower carbalkoxy; lower alkanoyl; arylyol; lower arylalkanoyl; carbamoyl; N-mono- or N,N-lower alkyl carbamoyl; lower alkyl carbamic acid ester; —NR₁₅R₁₆, wherein R₁₅ and R₁₆ can be the same or different and are independently H or lower alkyl; or R₁₅ and R₁₆ together with the N atom form a 3- to 8-membered heterocyclic ring containing 1-4 nitrogen, oxygen or sulfur ring atoms. The preferred value of M is hydrogen. The preferred values of R₁, R₂, R₃, n, Q, A, D, A₁ and Y described hereinabove are also applicable in this embodiment.

In an another embodiment, preferred are compounds of formula (II) or pharmaceutically acceptable salts thereof, wherein
R₁ is H or C₁-C₄ alkyl, which may be unsubstituted or substituted;
R₂ is H or C₁-C₄-alkyl, which may be unsubstituted or substituted;
R₃ is H or C₁-C₄ alkyl, which may be unsubstituted or substituted;
R₄ is cyclohexyl, isopropyl, which may be unsubstituted or substituted;
A is 5- or 6-membered nitrogen, oxygen or sulfur containing heteroaryl, which may be unsubstituted or substituted;
D is C(O), O, S(O)r or NR₇;
A₁ is aryl, which is substituted; and
n is as defined hereinabove.

The preferred definition of the various variables described hereinabove are also applicable in this embodiment. However, the preferred values of R₁ is H or methyl. In addition, the preferred value of R₂ is hydrogen or methyl. The preferred value of R₃ is hydrogen, ethyl or methyl.

It is preferred that n is 0, that is, the remaining substituents on the pyrrolindine ring are all hydrogens.

The preferred values of A is a 5- or 6-membered heteroaryl ring containing at least 1 nitrogen ring atom. Preferably, it contains 1 nitrogen ring atom and 4-5 carbon ring atoms or 2 ring heteroatoms and 3-4 ring carbon atoms, wherein 1 of the ring atoms is a nitrogen atom, and the other ring heteroatom is an oxygen, sulfur or nitrogen atom. Examples include pyridyl (e.g., 2-pyridyl, 3-pyridyl, or 4-pyridyl), pyrimidinyl, thiazolyl, oxazolyl and pyrrolyl, e.g., 2-pyrrolyl.

In an embodiment A₁ is substituted aryl, especially substituted phenyl, wherein the substituents are as defined hereinabove.

The preferred values of D is C(O), O, S, NR₇ and most especially C(O) or O.

Another embodiment is a compound of formula (I) has formula (IV):

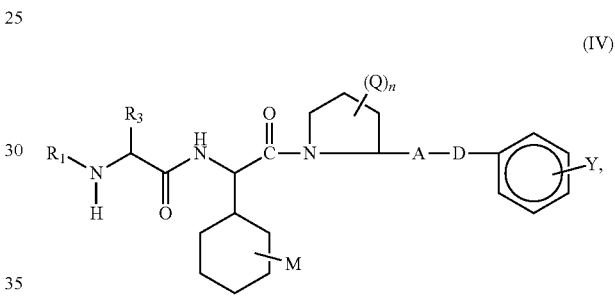

or pharmaceutically acceptable salts thereof,
wherein
R₁, R₃, Q, n, A₁, D, M are as defined hereinabove; and
Y is halo, lower alkoxy, NR₅R₆, CN, NO₂ or SR₅, wherein R₅ and R₆ are defined above.

In an embodiment, Y is halo. It is preferred that Y is on the para position. The preferred value of R₁, R₃, Q, n, A₁ and D described hereinabove are also applicable in this embodiment. It is most preferred that Y is fluorine.

A further embodiment is directed to compounds of the formula (V):

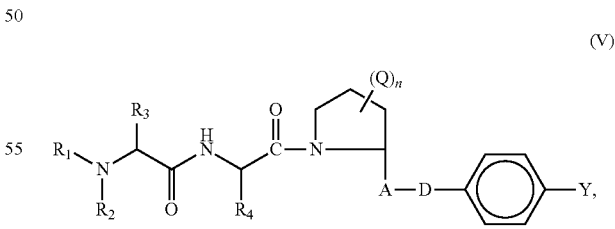

or pharmaceutically acceptable salts thereof,
wherein
R₂ is H;
R₄ is unsubstituted cyclohexyl; and
R₁, R₃, A, D and Y are as defined hereinabove.

The various values of R₁, R₃, A, D, Qn and Y described hereinabove are also applicable. In the compound of formula (V), in an embodiment, as described hereinabove, n is 0.

In a preferred embodiment of the present invention, $R_3$ and $R_4$ have the stereochemistry indicated in formula (VI), with the definitions of the various substituents described hereinabove with respect to formulae (I)-(V) also applying to compounds of formula (VI). Thus, another embodiment of the present invention is directed to compounds of formula (VI):

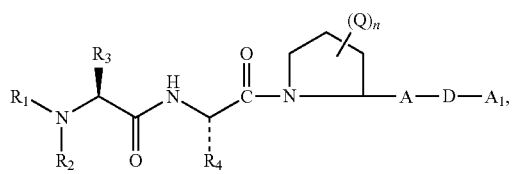

(VI)

or pharmaceutically acceptable salts thereof, wherein $R_1$, $R_2$, $R_3$, $R_4$, Q, n, A, D and $A_1$ are as defined in any of the embodiments hereinabove.

In another embodiment of the present invention, the compound of formula (VI) has the formula (VII):

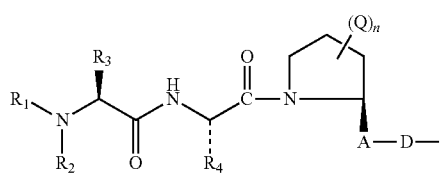

(VII)

or pharmaceutically acceptable salts thereof, wherein $R_1$, $R_2$, $R_3$, $R_4$, A, D, Q, $A_1$ and n are as defined hereinabove.

It is to be understood that the preferred values of the variables described hereinabove with respect to compounds of formulae (I)-(V) are also applicable to the compounds of formulae (VI) and (VII).

The compounds of the present invention are prepared by art recognized techniques. For example, compounds of formula (I) are prepared by reacting a carboxylic acid or acylating derivative thereof, such as an acid halide of formula (VIII) with an amine of formula (IX) under amide forming conditions:

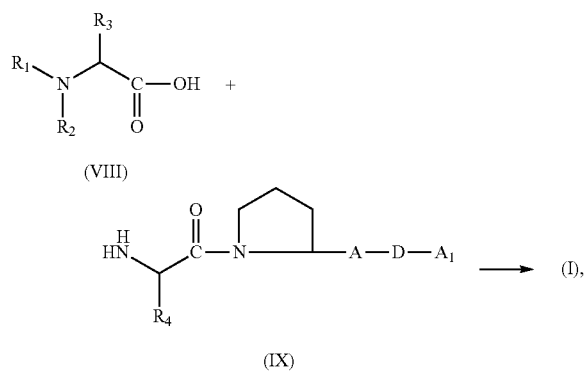

wherein $R_1$, $R_2$, $R_3$, $R_4$, Q, n, D, A and $A_1$ are as defined hereinabove or $R_1$, $R_2$ as an amino protecting group that is removed after the reaction is affected.

Alternatively, a compound of formula (I) may be prepared by reacting a carboxylic acid of formula (X) or acylating derivative thereof, such as acid halide, and the like with a pyrrolidine of formula (XI) under amide forming conditions:

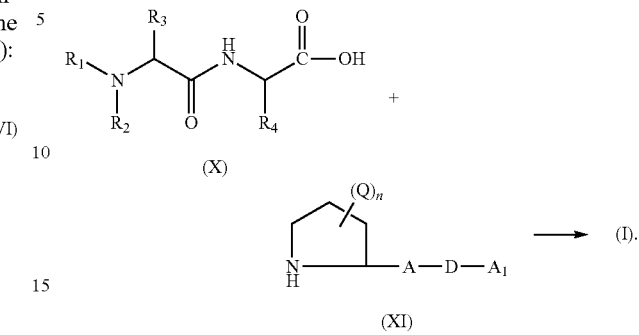

The above reactions are preferably conducted under effective conditions. For example, if the reactants of formulae (VIII) and (X) are acid halides, for instance, then they are reacted with compounds of formula (IX) or (XI), respectively, to form a compound of formula (I). Alternatively, the acid of formulae (VIII) and (X) is reacted with a compound of formulae (IX) and (XI), respectively, to generate a compound of formula (I) in the presence of a coupling reagent, such as HOBt, HBTU and the like, in the presence of a weak base, such as diethylamine and the like.

The compound of formula (VIII) is either commercially-available or prepared by art recognized procedures.

The compound of formula (IX) is also prepared under amide forming conditions by reacting a compound of formula (XIV) or acylating derivative thereof with a compound of formula (XI):

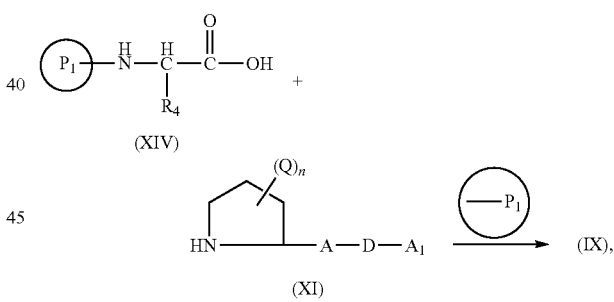

under amide forming conditions,
wherein
$P_1$ is an amide protecting group; and
$R_4$, Q, n, A, D and $A_1$ are as defined herein.

For example as described hereinabove, a compound of formula (XIV) is reacted with a compound of formula (XI) in the presence of a peptide coupling reagent known in the art, such as HOBt, HBTU, and the like in the presence of a weak base such as diethylamine and the like. Alternatively, if the acetylating derivative of compound of formula (XIV) were an acid halide, e.g., an acid chloride, then it would react with the amine of formula (XV), without the necessity of a coupling agent to form the compound of formula (I).

The compound of formula (XIV) is a protected amino acid and either commercially-available or is prepared from formula (XV):

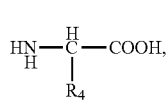

(XV)

in which the amino group is reacted with an amino protecting group under conditions known to one of ordinary skill in the art.

The compound of formula (XV) is either commercially-available or prepared under art recognized conditions.

The compound of formula (XI) is either commercially-available or may be prepared according to the scheme shown below.

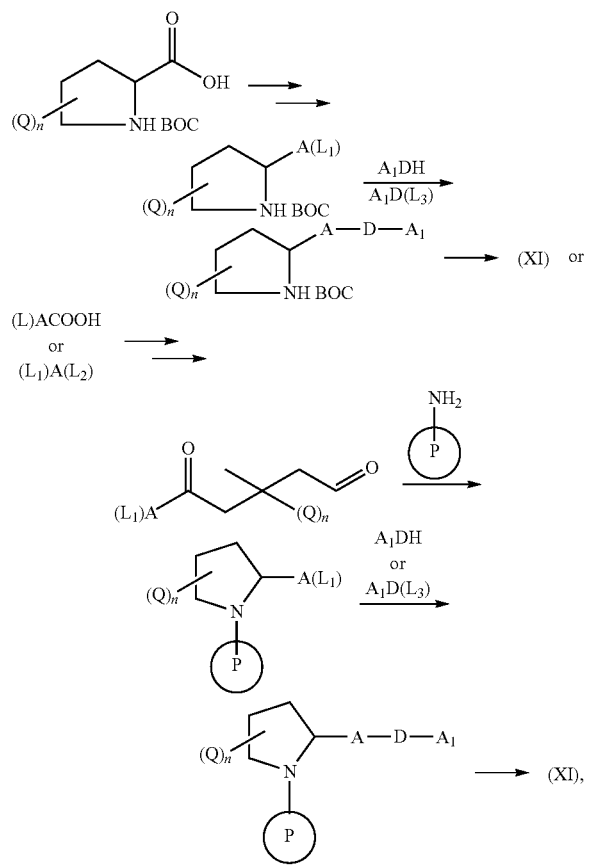

wherein

A, $A_1$, Q and n are as defined hereinabove;

$L_1$, $L_2$ and $L_3$ are leaving groups; and

is a protecting group and/or a chiral auxiliary.

The compound of formula (X) is prepared by art recognized techniques. For example, the compound of formula (VIII) or acylating derivative thereof is reacted with a compound of formula (XXI) under amide forming conditions:

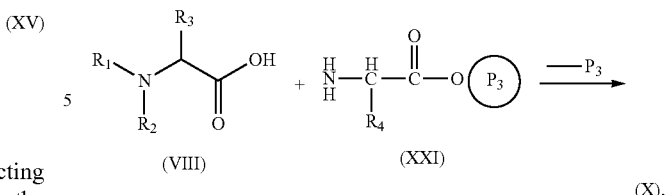

(X), wherein $R_1$, $R_2$, $R_3$, $R_4$ are as defined herein, or $R_1$, $R_2$ as an amino protecting group that is removed after the reaction is affected; and $P_3$ is a carboxylic acid protecting group.

The preparation of a compound of formula (VIII) is described hereinabove. The compound of formula (XXI) is derived from a compound of formula (XV), which is also described hereinabove.

Each of the reactions described hereinabove are preferably conducted in a solvent in which the reactants are soluble, such as methylene chloride, diethyl ether, and the like. In addition, the reactions are conducted at temperatures effective for the reactions to take place.

If any group on the reactants is reactive under the conditions described it is protected by a protecting group known in the art, prior to conducting the reactions described hereinabove and then removed after the reaction is effected. Protecting groups normally used in these reactions are described in a book entitled *Protective Groups in Organic Synthesis*, Theodora W. Greene, John Wiley & Sons, NY, N.Y. (1981), the contents of which are incorporated by reference.

As discussed above, the compounds of the present invention are useful for treating proliferative diseases. Thus, the present invention further relates to a method of treating an animal having a proliferative disease which comprises administering a therapeutically effective amount of a compound of formulae (I)-(VII) to a mammal, preferably a human, in need of such treatment.

The term a "therapeutically effective amount" or synonym thereto of the compound of formulae (I)-(VII), as defined herein, is that amount sufficient to effect beneficial or desired results, including clinical results. For example, when referring to an agent that inhibits cell poliferatrion, a therapeutically effective amount of the compound of formulae (I)-(VII) is, e.g., that amount sufficient to achieve such a reduction in cancer cell proliferation as compared to the response obtained in the absence of (or without administering) the compound of formulae (I)-(VII).

As used herein, and as well understood in the art, "treatment" is an approach for obtaining beneficial or desired results including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total) whether detectable or undectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate", as used herein, includes the inhibition or suppression of a function or activity (such as cell proliferation) as well as the enhancement of a function or activity.

To "inhibit" or "suppress" or "reduce" a function or activity, such as cancer cell proliferation, is to reduce the function or activity when compared to otherwise same conditions except for a condition or parameter of interest, or alternatively, as compared to another conditions.

The term "animal", as used herein, includes all members of the animal kingdom including humans and non-humans. The animal is preferably a human.

The term "a cell", as used herein, includes a plurality of cells. Administering a compound to a cell includes in vivo, ex vivo and in vitro treatment.

The term "cancer cells", as used herein, includes all forms of cancer or neoplastic disease.

A proliferative disease is mainly a tumor or cancer and/or any metastases. The compounds of the present invention are particularly useful for treating a cancer, e.g., breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular, (i) a breast tumor; an epidermoid tumor, such as an epidermoid head and/or neck tumor or a mouth tumor; a lung tumor, e.g., a small cell or non-small cell lung tumor; a gastrointestinal tumor, e.g., a colorectal tumor; or a genitourinary tumor, e.g., a prostate tumor (especially a hormone-refractory prostate tumor); (ii) a proliferative disease that is refractory to the treatment with other chemotherapeutics; or (iii) a tumor that is refractory to treatment with other chemotherapeutics due to multidrug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are also implied.

The compounds of formulae (I)-(VII) selectively toxic or more toxic to rapidly proliferating cells than to normal cells, particularly in human cancer cells, e.g., cancerous tumors. In addition, the compounds of formulae (I)-(VII) have significant antiproliferative effects and promotes differentiation, e.g., cell cycle arrest and apoptosis.

The present invention further relates to a method of promoting apoptosis in rapidly proliferating cells, which comprises contacting the rapidly proliferating cells with an effective apoptosis promoting amount of a non-naturally-occurring compound that binds to the Smac binding site of XIAP and/or cIAP proteins. Preferably, the non-naturally-occurring compound is a compound of formulae (I)-(VII).

In accordance with a further aspect of the present invention, there is provided a method for modulating cell proliferation, preferably inhibiting cell proliferation comprising administering an effective amount of a compound of formulae (I)-(VII) to a cell or animal in need thereof. The invention also includes a use of a compound of formulae (I)-(VII) to modulate cell proliferation, preferably inhibit cell proliferation. The invention further includes a use of a compound of the invention to prepare a medicament to modulate cell proliferation, preferably inhibit cell proliferation.

In one aspect, the present invention provides a method for modulating cell proliferation comprising administering an effective amount of a compound of formulae (I)-(VII) to a cell or animal in need thereof. Preferably, the invention provides a method of inhibiting cell proliferation comprising administering an effective amount of a compound of formulae (I)-(VII) to a cell or animal in need thereof. In particular, the method of the invention is useful in inhibiting the proliferation of abnormal but not normal cells. Abnormal cells include any type of cell that is causative of or involved in a disease or condition and wherein it is desirable to modulate or inhibit the proliferation of the abnormal cell to treat the disease or condition. Examples of abnormal cells include malignant or cancerous cells.

The invention also includes a use of a compound of the invention of formulae (I)-(VII) to modulate cancer cell proliferation, preferably to inhibit cancer cell proliferation. The invention further includes a use of a compound of the invention to prepare a medicament to modulate cancer cell proliferation, preferably inhibit cancer cell proliferation.

It has been determined that the compounds of the present invention of formulae (I)-(VII) are very effective at killing cancer cells while at the same time they do not kill normal cells. These properties make the compounds of the present invention extremely useful as anti-cancer agents. Accordingly, in one embodiment, the present invention provides a method of inhibiting the proliferation of a cancer cell comprising administering an effective amount of a compound formulae (I)-(VII) to a cell or animal in need thereof.

In a preferred embodiment the present invention provides a method of inhibiting the proliferation of a cancer cell comprising administering an effective amount of a compound of the invention of formulae (I)-(VII) to a cell or animal in need thereof. The cancer cell treated may be any type of cancer including but not limited to hematopoictic malignancies, including, a leukemia, a lymphoma, myeloma, metastatic carcinoma, sarcoma, adenomas, nervous system cancers and geritourinary cancers, or any other malignant transformation or any other malignancy. As hereinbefore mentioned, the inventors have prepared novel compounds of formulae (I)-(VII). Accordingly, the present invention includes all uses of the compounds of the invention including their use in therapeutic methods and compositions for modulating cell proliferation, their use in diagnostic assays and their use as research tools.

Examples of leukemias include acute lymphoblastic leukemia (ALL), acute myelocytic leukemia (AML), chronic myeloid leukemia (CML), chronic lymphocytic leukemia (CLL) and juvenile myelo-monocytic leukemia (JMML). The types of ALL that may be treated with the compounds of the invention include cells that express a bcr-abl fusion protein, such as Philadelphia positive ALL cells, as well as Philadelphia negative ALL cells. Examples of lymphomas include B-cells Burkitts lymphobia, Hidgkin's lymphomas, non-Hodgkin's lymphomas, including the Ki-I positive an a plastic cell lymphomas, T-cell lymphomas and rare lymphomas such as histiocytic lymphomas. Examples of myelomas include multiple myelomas.

The present invention further relates to a method of treating or inhibiting myeloma, especially multiple myeloma. The term "myeloma", as used herein, relates to a tumor composed of cells of the type normally found in the bone marrow. The term "multiple myeloma", as used herein, means a disseminated malignant neoplasm of plasma cells which is characterized by multiple bone marrow tumor foci and secretion of an M component (a monoclonal immunoglobulin fragment), associated with widespread osteolytic lesions resulting in bone pain, pathologic fractures, hypercalcaemia and normochromic normocytic anaemia. Multiple myeloma is incurable by the use of conventional and high dose chemotherapies. The invention relates to a method of treating a patient having a myeloma, especially myeloma which is resistant to conventional chemotherapy, by administering to the patient an antitumor effective amount of a compound of any formulae (I)-(VII).

Pharmaceutical Compositions

The present invention relates also to pharmaceutical compositions comprising a compound of formulae (I)-(VII), to their use in the therapeutic (in a broader aspect of the invention also prophylactic) treatment or a method of treatment of a kinase dependent disease, especially the preferred diseases mentioned above, to the compounds for said use and to pharmaceutical preparations and their manufacture, especially for said uses.

The present invention also relates to pro-drugs of a compound of formulae (I)-(VII) that convert in vivo to the compound of formulae (I)-(VII) as such. Any reference to a compound of formulae (I)-(VII) is therefore to be understood as referring also to the corresponding pro-drugs of the compound of formula (I), as appropriate and expedient.

The pharmacologically acceptable compounds of the present invention may be present in or employed, e.g., for the preparation of pharmaceutical compositions that comprise an effective amount of a compound of the formulae (I)-(VII), or a pharmaceutically acceptable salt thereof, as active ingredient together or in admixture with one or more inorganic or organic, solid or liquid, pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g., lymphocytes), for the treatment of a disease that responds to inhibition of protein kinase activity, comprising an amount of a compound of formulae (I)-(VII) or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, of a compound of formulae (I)-(VII) or pharmaceutically acceptable salt thereof, in association with a pharmaceutically acceptable carrier. The dose of the active ingredient depends on the species of warm-blooded animal, the body weight, the age, the individual condition, individual pharmacokinetic data, the disease to be treated and the mode of administration.

The present invention relates also to a method of treatment for a disease that responds to inhibition of a protein kinase and/or a proliferative disease, which comprises administering (against the mentioned diseases) a therapeutically effective amount of a compound of formulae (I)-(VII) or pharmaceutically acceptable salt thereof according to the invention, or a tautomer thereof or a pharmaceutically acceptable salt thereof, especially to a warm-blooded animal, e.g., a human, that, on account of one of the mentioned diseases, requires such treatment.

The dose of a compound of the formulae (I)-(VII) or a pharmaceutically acceptable salt thereof to be administered to warm-blooded animals, e.g., humans of approximately 70 kg body weight, preferably is from approximately 3 mg to approximately 10 g, more preferably from approximately 10 mg to approximately 1.5 g, most preferably from about 100 mg to about 1,000 mg/person/day, divided preferably into 1-3 single doses which may, e.g., be of the same size or in sustained release form to obtain the desired results. Usually, children receive half of the adult dose.

The pharmaceutical compositions comprise form approximately 1% to approximately 95%, preferably from approximately 20% to approximately 90% of a compound of formulae (I)-(VII). Pharmaceutical compositions according to the invention may be, e.g., in unit dose form, such as in the form of ampoules, vials, suppositories, dragées, tablets or capsules.

The pharmaceutical compositions of the present invention are prepared in a manner known per se, e.g., by means of conventional dissolving, lyophilizing, mixing, granulating or confectioning processes.

In the treatment methods and compositions of the present invention, the active ingredient described in detail herein is (are) typically administered for oral, topical, rectal, parenteral, local, inhalant or intracerebral use. In an embodiment of the invention, the substances are administered in intranasal form via topical use of suitable intranasal vehicles, or via transdermal routes, using forms of transdermal skin patches known to those of ordinary skill in that art. To be administered in the form of a transdermal delivery system, the dosage administration will be continuous rather than intermittent throughout the dosage regimen. The substances can also be administered by way of controlled or slow release capsule system and other drug delivery technologies.

A preferred form of administration is oral. For example, for oral administration in the form of a tablet or capsule, the active substance(s) can be combined with an oral, non-toxic, pharmaceutically acceptable, inert carrier, such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and colouring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum and the like.

Gelatin capsules may contain the active substance and powdered carriers, such as lactose, starch, cellulose derivatives, magnesium stearate, stearic acid and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain colouring and flavouring agents to increase patient acceptance.

Water, a suitable oil, saline, aqueous dextrose, and related sugar solutions and glycols, such as propylene glycol or polyethylene glycols, may be used as carriers for parenteral solutions. Such solutions also preferable contain a water soluble salt of the active ingredient, suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and cholorobutanol.

The active ingredient described in detail herein can also be administered in the form of liposome delivery systems, such as small unilamellar vesicles, large unilamellar vesicles, and multilamellar resides. Liposomes can be formed from a variety of phospholipids, such as cholesterol, stearylamine or phosphatidyl cholines and the like.

As herein before mentioned, the present invention is directed to novel compounds of formulae (I)-(VII) or their pharmaceutically acceptable salts thereof. Accordingly, the present invention include all uses of the compound of the invention including their use in therapeutic methods and compositions for modulating cell proliferation, their use in diagnostic assays and their use as research tools.

The compounds of formulae (I)-(VII) described in detail herein may also be coupled with soluble polymers which are targetable drug carriers. Examples of such polymers include polyvinylpyrrolidone, pyran copolymer, polyhydroxypropylmethacrylamide-phenol, polydroxyethylaspartamidephenol, or polyethyleneoxide-polylysine substituted with palmitoyl residues. The active ingredient substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyortoesters, polyacetals, polydihydropyrans, polycyanoacylates, and crosslinked or amphipathic block copolymers of hydrogels. The substances can also be affixed to rigid polymers and other structures such as fullerenes or Buckeyballs.

Pharmaceutical compositions suitable for administration contain about 1-1,500 mg of compounds of formulae (I)-(VII) per unit. In these pharmaceutical compositions, the active ingredient will ordinarily be present in an amount of about 0.5-95% by weight based on the total weight of the composition.

Suitable pharmaceutical carriers and methods of preparing pharmaceutical dosage forms are described in Remington's Pharmaceutical Sciences, Mack Publishing Company, a standard reference text in art of drug formulation.

The compounds of the present invention may be administered alone or in combination with other anticancer agents, such as compounds that inhibit tumor angiogenesis, e.g., the protease inhibitors, epidermal growth factor receptor kinase inhibitors, vascular endothelial growth factor receptor kinase inhibitors and the like; cytotoxic drugs, such as antimetabolites, like purine and pyrimidine analog antimetabolites; antimitotic agents like microtubule stabilizing drugs and antimitotic alkaloids; platinum coordination complexes; anti-tumor antibiotics; alkylating agents, such as nitrogen mustards and nitrosoureas; endocrine agents, such as adrenocorticosteroids, androgens, anti-androgens, estrogens, anti-estrogens, aromatase inhibitors, gonadotropin-releasing hormone agonists and somatostatin analogues and compounds that target an enzyme or receptor that is overexpressed and/or otherwise involved a specific metabolic pathway that is upregulated in the tumor cell, e.g., ATP and GTP phosphodiesterase inhibitors, histone deacetylase inhibitors, protein kinase inhibitors, such as serine, threonine and tyrosine kinase inhibitors, e.g., Abelson protein tryosine kinase and the various growth factors, their receptors and kinase inhibitors therefore, such as, epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors and the like; methionine aminopeptidase inhibitors, proteasome inhibitors, and cyclooxygenase inhibitors, e.g., cyclooxygenase-1 or -2 inhibitors.

Combinations

A compound of formulae (I)-(VII) or pharmaceutically acceptable salts thereof may also be used to advantage in combination with other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further antiangiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

A compound of the formula (I) may also be used to advantage in combination with known therapeutic processes, e.g., the administration of hormones or especially radiation.

A compound of formula (I) may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g., synergistic, effect or any combination thereof.

EXAMPLES

The following examples are intended to illustrate, but not further limit, the invention.

Example 1

(S)—N—((S)-1-Cyclohexyl-2-{(S)-2-[4-(4-fluorobenzoyl)-thiazol-2-yl]-pyrrolidin-1-yl}-2-oxo-ethyl)-2-methylamino-propionamide The title compound, herein after, Compound A, is prepared by the following reaction scheme:

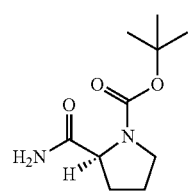
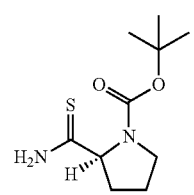
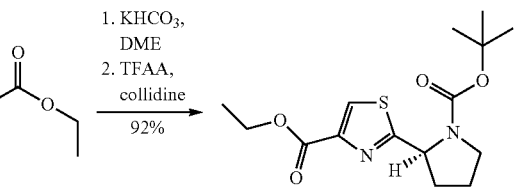
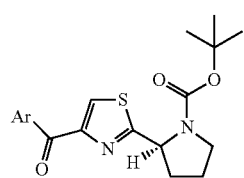
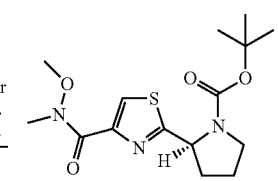
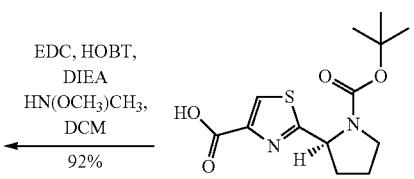
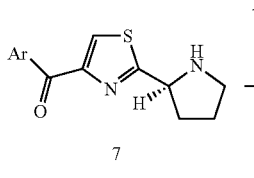
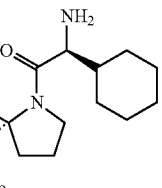
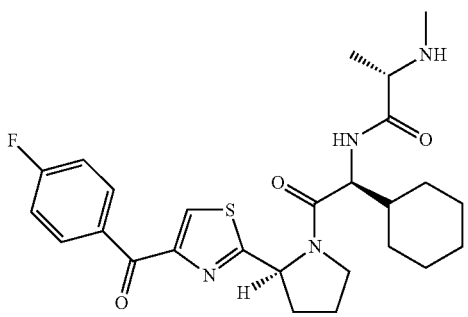

Step 1: Thioamdie (1)

Lawesson's Reagent (13.9 g, 34 mmol, 0.70 equiv.) is added portionwise (3×4.6 g) over 20 minutes to a solution of Boc-L-Pro (10.5 g, 49 mmol, 1 equiv.) in 70 mL of THF at 23° C. The resulting cloudy yellow mixture is stirred vigorously for 5 hours, then is concentrated to a light yellow solid. This residue is partitioned between ethyl acetate (300 mL) and saturated aqueous sodium bicarbonate solution (500 mL). The organic phase is separated and the aqueous phase is further extracted with ethyl acetate (2×500 mL). The organic phases are combined, washed with brine (500 mL), and dried over anhydrous sodium sulfate. The dried solution is filtered and concentrated to a light yellow solid. This solid is triturated with dichloromethane (2×20 mL) affording the desired thioamide 1 as a fluffy white solid (10 g, 89%).

Step 2: Thiazole (3)

Ethyl bromopyruvate (2) (23.8 mL, 189 mmol, 3 equiv.) is added dropwise via syringe to a mixture of the thioamide (1) (14.5 g, 63.0 mmol, 1 equiv.) and potassium bicarbonate (50.5 g, 504 mmol, 8 equiv.) in 315 mL of dimethoxyethane at 23° C. The mixture turned yellow upon addition which was complete within 5 minutes. The resulting mixture is stirred vigorously for 25 minutes, then is cooled to 0° C. A neat mixture of trifluoroacetic anhydride (TFAA) (8.8 mL, 63 mmol, 1 equiv.) and collidine (13.5 mL, 102 mmol, 1.6 equiv.) is added dropwise via canula to the yellow mixture prepared above at 0° C. Following this addition, an additional three portions of neat TFAA (8.8 mL, 63 mmol, 1 equiv.) and collidine (13.5 mL, 102 mmol, 1.6 equiv.) are prepared and added in sequence dropwise via canula to the yellow reaction mixture at 0° C. The resulting yellow mixture is stirred vigorously at 0° C. for 3 hours, then water (1,000 mL) is added. The resulting solution is extracted with dichloromethane (2×500 mL). The organic phases are combined, washed with 0.5 N aqueous HCL solution (500 mL), washed with brine (500 mL), and dried over anhydrous sodium sulfate. The dried solution is filtered and concentrated to a light yellow solid. This solid is purified by flash column chromatography (1:9 to 2:3 ethyl acetate:hexanes) providing a light yellow solid. Trituration of this solid with ether (20 mL) afforded the thiazole (3) as a white solid (19 g, 92%).

Step 4: Acid (4)

A solution of the thiazole (3) (5 g, 15.3 mmol, 1 equiv.) in tetrahydrofuran (40 mL) is added to a solution of sodium hydroxide (3.68 g, 91.9 mmol, 6 equiv.) in water (40 mL) at 23° C. The resulting mixture is stirred vigorously at 23° C. for 3 hours, then is concentrated to 20 mL. The concentrated mixture is cooled to 0° C. and the pH is adjusted to 3 by the dropwise addition of concentrated HCl solution. The white solid is collected by filtration to provide the desired carboxylic acid (4) as a white solid (4.3 g, 94%).

Step 5: Weinreb Amide (5)

HBTU (21 g, 55.5 mmol, 1.5 equiv.) is added to a solution of the acid (4) (11 g, 37 mmol, 1 equiv.) in DMF (100 mL) at 23° C. The resulting mixture is cooled to 0° C. DIEA (32.2 mL, 185 mmol, 5 equiv.) and N,O-dimethylhydroxylamine hydrochloride (4.33 g, 44.4 mmol, 1.2 equiv.) are added in sequence to the reaction mixture prepared above at 0° C. The resulting mixture is allowed to stir at 0° C. for 1 hour, then at 23° C. for 3 hours. The reaction is then concentrated to a brown oil. This residue is partitioned between ethyl acetate (500 mL) and water (1 L). The organic phase is separated and the aqueous phase is further extracted with ethyl acetate (2×500 mL). The organic phases are combined, washed with saturated sodium bicarbonate solution (500 mL), washed with 5% citric acid solution (500 mL), washed with brine (500 mL) and dried over anhydrous sodium sulfate. The dried solution is filtered and concentrated to a light yellow solid. This solid is purified by flash column chromatography (1:9 to 9:1 ethyl acetate:hexanes) providing the weinreb amide (5) as a light yellow solid (11.1 g, 92%)

Step 6: Ketone (6)

4-Fluorophenyl magnesium bromide (0.8 M in THF, 27.5 mL, 22 mmol, 3 equiv.) is added dropwise via syringe to a solution of the weinreb amide (5) (2.5 g, 7.32 mmol, 1 equiv.) in THF (70 mL) at −55° C. (dry ice/isopropanol bath). The mixture is stirred at −55° C. for 1 hour, then an additional portion of 4-fluorophenyl magnesium bromide (0.8 M in THF, 27.5 mL, 22 mmol, 3 equiv.) is added to drive the reaction to completion. The resulting mixture is allowed to warm to −10° C. over 2 hours and was stirred at that temperature for an additional 30 minutes. The mixture is then cooled to −55° C. and saturated ammonium chloride solution (50 mL) is added dropwise via syringe. The mixture was partitioned between water (1 L) and ethyl acetate (250 mL). The organic phase is separated and the aqueous phase is further extracted with ethyl acetate (2×250 mL). The organic phases are combined, washed with brine (500 mL) and dried over anhydrous sodium sulfate. The dried solution is filtered and concentrated to a light yellow oil. This oil is purified by flash column chromatography (1:9 to 3:7 ethyl acetate:hexanes) providing the ketone (6) as a clear oil (2.3 g, 83%).

The rest of the synthesis follows procedures that were disclosed in WO 05/097791 which published Oct. 20, 2005, resulting in Compound A: MS ESI 501.23 (M+H)$^+$.

Example 2

(S)—N-[(S)-Cyclohexyl-(ethyl-{(S)-1-[5-(4-fluoro-benzoyl)-pyridin-3-yl]-propyl}-carbamoyl)-methyl]-2-methylamino-propionamide The title compound, hereinafter referred to as Compound B, is prepared by the following reaction scheme:

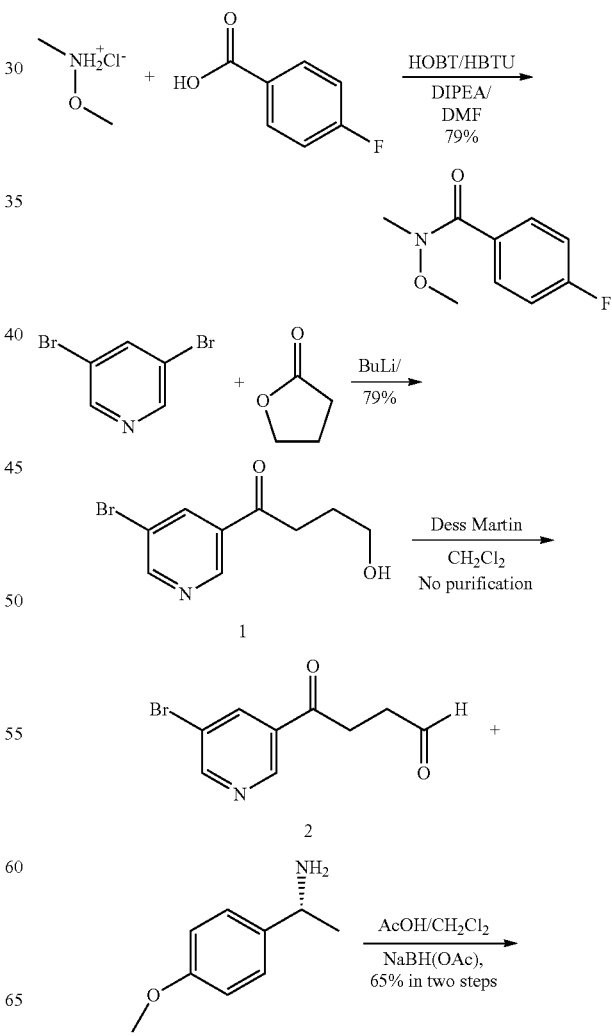

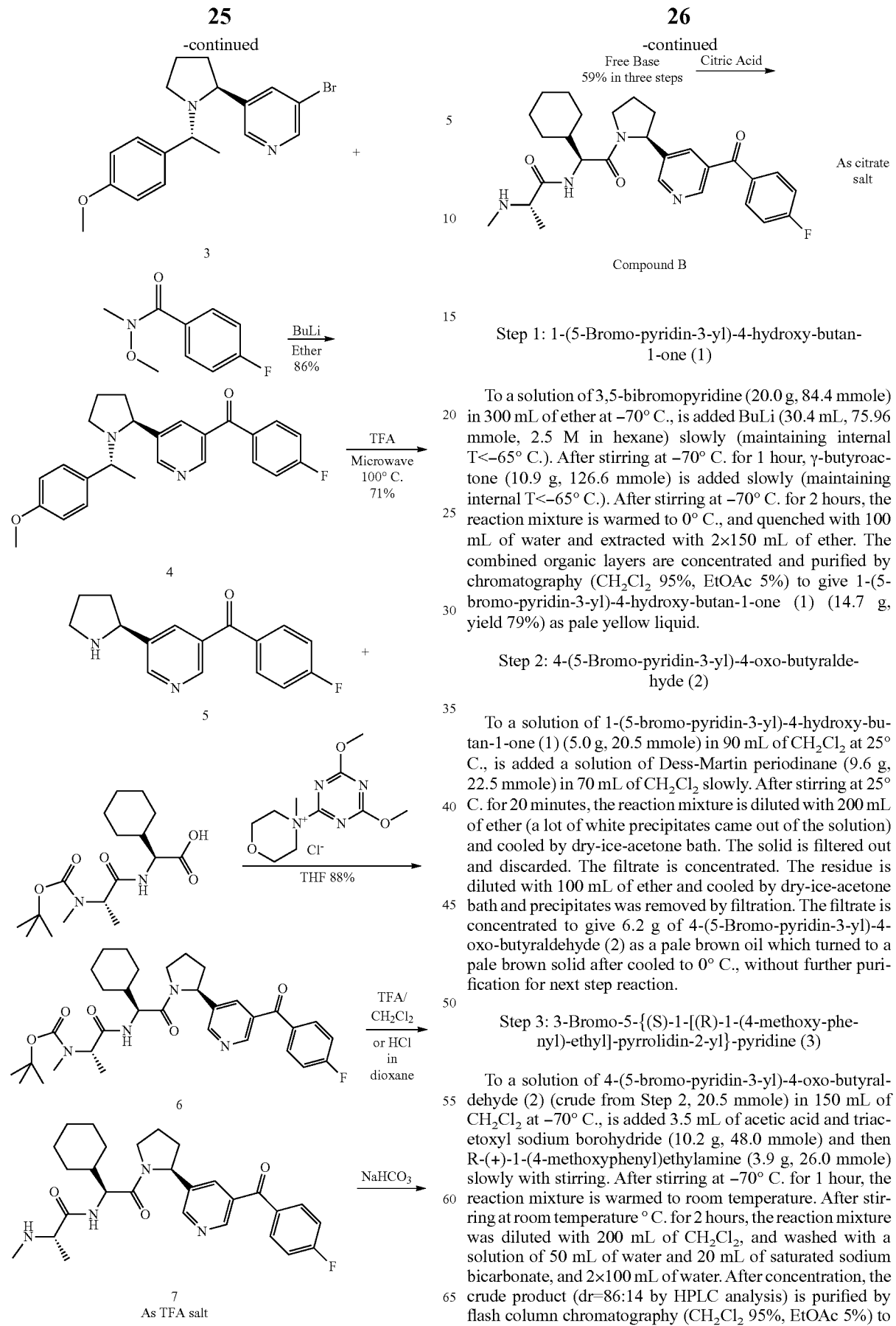

Step 1: 1-(5-Bromo-pyridin-3-yl)-4-hydroxy-butan-1-one (1)

To a solution of 3,5-bibromopyridine (20.0 g, 84.4 mmole) in 300 mL of ether at −70° C., is added BuLi (30.4 mL, 75.96 mmole, 2.5 M in hexane) slowly (maintaining internal T<−65° C.). After stirring at −70° C. for 1 hour, γ-butyroactone (10.9 g, 126.6 mmole) is added slowly (maintaining internal T<−65° C.). After stirring at −70° C. for 2 hours, the reaction mixture is warmed to 0° C., and quenched with 100 mL of water and extracted with 2×150 mL of ether. The combined organic layers are concentrated and purified by chromatography (CH$_2$Cl$_2$ 95%, EtOAc 5%) to give 1-(5-bromo-pyridin-3-yl)-4-hydroxy-butan-1-one (1) (14.7 g, yield 79%) as pale yellow liquid.

Step 2: 4-(5-Bromo-pyridin-3-yl)-4-oxo-butyraldehyde (2)

To a solution of 1-(5-bromo-pyridin-3-yl)-4-hydroxy-butan-1-one (1) (5.0 g, 20.5 mmole) in 90 mL of CH$_2$Cl$_2$ at 25° C., is added a solution of Dess-Martin periodinane (9.6 g, 22.5 mmole) in 70 mL of CH$_2$Cl$_2$ slowly. After stirring at 25° C. for 20 minutes, the reaction mixture is diluted with 200 mL of ether (a lot of white precipitates came out of the solution) and cooled by dry-ice-acetone bath. The solid is filtered out and discarded. The filtrate is concentrated. The residue is diluted with 100 mL of ether and cooled by dry-ice-acetone bath and precipitates was removed by filtration. The filtrate is concentrated to give 6.2 g of 4-(5-Bromo-pyridin-3-yl)-4-oxo-butyraldehyde (2) as a pale brown oil which turned to a pale brown solid after cooled to 0° C., without further purification for next step reaction.

Step 3: 3-Bromo-5-{(S)-1-[(R)-1-(4-methoxy-phenyl)-ethyl]-pyrrolidin-2-yl}-pyridine (3)

To a solution of 4-(5-bromo-pyridin-3-yl)-4-oxo-butyraldehyde (2) (crude from Step 2, 20.5 mmole) in 150 mL of CH$_2$Cl$_2$ at −70° C., is added 3.5 mL of acetic acid and triacetoxyl sodium borohydride (10.2 g, 48.0 mmole) and then R-(+)-1-(4-methoxyphenyl)ethylamine (3.9 g, 26.0 mmole) slowly with stirring. After stirring at −70° C. for 1 hour, the reaction mixture is warmed to room temperature. After stirring at room temperature ° C. for 2 hours, the reaction mixture was diluted with 200 mL of CH$_2$Cl$_2$, and washed with a solution of 50 mL of water and 20 mL of saturated sodium bicarbonate, and 2×100 mL of water. After concentration, the crude product (dr=86:14 by HPLC analysis) is purified by flash column chromatography (CH$_2$Cl$_2$ 95%, EtOAc 5%) to give 3-bromo-5-{(S)-1-[(R)-1-(4-methoxy-phenyl)-ethyl]- pyrrolidin-2-yl}-pyridine (3) (4.7 g, yield 65% in two steps) as a light brown viscose liquid.

Step 4a: 4-Fluoro-N-methoxy-N-methyl-benzamide (4a)

To a solution of 4-fluorobenzoic acid (6.8 g, 48.57 mmole) in 100 mL of DMF at room temperature, is added diisopropylethylamine (25.3 mL, 145.7 mmole). After stirring at room temperature for 20 minutes, HOBT (7.22 g, 53.43 mmole), HBTU (20.26 g, 53.43 mmole) and N,O-dimethyl hydroxylamine hydrochloride (5.69 g, 58.29 mmole) are added to the reaction solution. After stirring at room temperature for 2 hours, the reaction solution is diluted with 200 mL of EtOAc and washed with 4×50 mL of water. The combined organic layers is concentrated and purified by flash column chromatography (hexane 70%, EtOAc 30%) to yield 4-fluoro-N-methoxy-N-methyl-benzamide (4a) (7.0 g, yield 79%).

Step 4: (4-Fluoro-phenyl)-(5-{(S)-1-[(R)-1-(4-methoxy-phenyl)-ethyl]-pyrrolidin-2-yl}-pyridin-3-yl)-methanone (4)

To a solution of 3-bromo-5-{(S)-1-[(R)-1-(4-methoxy-phenyl)-ethyl]-pyrrolidin-2-yl}-pyridine (3) (6.0 g, 16.6 mmole) in 100 mL of ether at −73° C., is added a solution of butyl lithium (7.3 mL, 18.3 mmole, 2.5 M in hexane) slowly (maintaining internal T<−70° C.). After stirring at −73° C. for 30 minutes, a solution of 4-fluoro-N-methoxy-N-methyl-benzamide (4a) (4.56 g, 24.9 mmole) in 15 mL of ether is added slowly (maintaining internal T<−70° C.). After stirring at −70° C. for 1.5 hours, the reaction is quenched by addition of 20 mL of water and warmed to room temperature with stirring. The resulting mixture is diluted with 100 mL of EtOAc and washed with 2×30 mL of water. The organic layer is concentrated and purified by flash column chromatography ($CH_2Cl_2$ 95%, EtOAc 5%) to give (4-fluoro-phenyl)-(5-{(S)-1-[(R)-1-(4-methoxy-phenyl)-ethyl]-pyrrolidin-2-yl}-pyridin-3-yl)-methanone (4) (6.4 g, yield 86%) as a light brown viscose liquid.

Step 5: 4-Fluoro-phenyl)-((S)-5-pyrrolidin-2-yl-pyridin-3-yl)-methanone (5)

A solution of (4-fluoro-phenyl)-(5-{(S)-1-[(R)-1-(4-methoxy-phenyl)-ethyl]-pyrrolidin-2-yl}-pyridin-3-yl)-methanone (4) (3.3 g, 8.17 mmole) in 5 mL of TFA is heated at 100° C. in a microwave reactor for 30 minutes. The result solution is concentrated to remove TFA. The residue is diluted with 100 mL of $CH_2Cl_2$, and basified by washing with 5 mL of saturated sodium bicarbonate. The organic layer is concentrated and purified by flash column chromatography ($CH_2Cl_2$ 100% to $CH_2Cl_2$ 80% MeOH 20% gradient in 30 minutes) to give 4-fluoro-phenyl)-((S)-5-pyrrolidin-2-yl-pyridin-3-yl)-methanone (5) (1.57 g, yield 71%) as a light brown viscose liquid.

Step 6: (S)-1-((S)-1-Cyclohexyl-2-{(S)-2-[5-(4-fluoro-benzoyl)-pyridin-3-yl]-pyrrolidin-1-yl}-2-oxo-ethylcarbamoyl)-ethyl]-methyl-carbamic acid tert-butyl ester (6)

To a solution of 4-fluoro-phenyl)-((S)-5-pyrrolidin-2-yl-pyridin-3-yl)-methanone (2.57 g, 9.5 mmole) and (S)-[(S)-2-(tert-butoxycarbonyl-methyl-amino)-propionylamino]-cyclohexyl-acetic acid (5) (3.58 g, 10.5 mmole) in 75 mL of THF at 0° C., is added 4-(4,6-dimethoxy-[1,3,5]triazin-2-yl)-4-methyl-morpholinium chloride hydrate (2.97 g, 10.7 mmole) in one portion. After stirring at 20° C. for 2 hours, the reaction mixture is diluted with 100 mL of EtOAc, and washed with 3×20 mL of water. After concentration, the crude product is purified by flash column chromatography ($CH_2Cl_2$ 95%, MeOH 5%) to give (S)-1-((S)-1-cyclohexyl-2-{(S)-2-[5-(4-fluoro-benzoyl)-pyridin-3-yl]pyrrolidin-1-yl}-2-oxo-ethylcarbamoyl)-ethyl]-methyl-carbamic acid tert-butyl ester (6) (5.0 g, yield 88%) as pale yellow solid.

Step 7: (S)—N—((S)-1-Cyclohexyl-2-{(S)-2-[5-(4-fluoro-benzoyl)-pyridin-3-yl]-pyrrolidin-1-yl}-2-oxo-ethyl)-2-methylamino-propionamide dihydrotrifluoroacetate (7)

To a solution of (S)-1-((S)-1-cyclohexyl-2-{(S)-2-[5-(4-fluoro-benzoyl)-pyridin-3-yl]-pyrrolidin-1-yl}-2-oxo-ethylcarbamoyl)-ethyl]-methyl-carbamic acid tert-butyl ester (6) (4.78 g, 8.05 mmole) in 3 mL of $CH_2Cl_2$ at −20° C., is added 10 mL of TFA (pre-cooled to −20° C.) slowly. After stirring at 0° C. for 30 minutes, the reaction mixture is concentrated to remove TFA as much as possible at room temperature under high vacuum. The crude product is purified by reversed phase HPLC (Column: Waters Sunfire, 50×50 mm; mobile phase: $CH_3CN$ 25% $H_2O$ 75% with 0.1% TFA to $CH_3CN$ 45% $H_2O$ 55% with 0.1% TFA by gradient in 8 minutes; flow rate 65 mL/minute; detector: 215 nm UV) to give (S)—N—((S)-1-cyclohexyl-2-{(S)-2-[5-(4-fluoro-benzoyl)-pyridin-3-yl]-pyrrolidin-1-yl}-2-oxo-ethyl)-2-methylamino-propionamide dihydrotrifluoroacetate (7) (3.4 g, 4.70 mmol, 58% based on 2 TFA salt) as colorless glassy solid.

An alternative procedure for Boc deprotection of Compound B employs HCl in dioxane instead of TFA: 3.38 g of dipeptide-coupled product is dissolved in 50 mL of $CH_2Cl_2$ at −30° C. 8 mL HCl in dioxane (4.0 M) was added slowly and reaction was stirred at −30° C. for 30 minutes. The bath was then removed and the reaction warmed to room temperature over 2 hours. By LC/MS, the reaction was complete at 2.5 hours. Evaporate the solvent to dryness to get an oil, which is then purified on the HPLC. The yield is 70-81%.

Step 8: (S)—N—((S)-1-Cyclohexyl-2-{(S)-2-[5-(4-fluoro-benzoyl)-pyridin-3-yl]-pyrrolidin-1-yl}-2-oxo-ethyl)-2-methylamino-propionamide citrate (Compound B)

The TFA salt, (S)—N—((S)-1-cyclohexyl-2-{(S)-2-[5-(4-fluoro-benzoyl)-pyridin-3-yl]-pyrrolidin-1-yl}-2-oxo-ethyl)-2-methylamino-propionamide dihydrotrifluoroacetate (7) (3.4 g) is dissolved in 50 mL of $CH_2Cl_2$, and basified by saturated sodium bicarbonate to pH=8. The solution of free base is washed with 2×5 mL of water and dried over sodium sulfate, and is concentrated to give (S)—N—((S)-1-cyclohexyl-2-{(S)-2-[5-(4-fluoro-benzoyl)-pyridin-3-yl]-pyrrolidin-1-yl}-2-oxo-ethyl)-2-methylamino-propionamide (2.37 g, 4.80 mmole) which is dissolved in a solution of citric acid (901 mg, 4.80 mmole) in 200 mL of water. The solution was dried by freeze dryer to give (S)—N—((S)-1-cyclohexyl-2-{(S)-2-[5-(4-fluoro-benzoyl)-pyridin-3-yl]-pyrrolidin-1-yl}-2-oxo-ethyl)-2-methylamino-propionamide citrate, Compound B, (3.23 g, yield 59% in three steps from compound 6) as light yellow solid. MS ESI 495.27 $(M+H)^+$.

Example 3

(S)—N—((S)-1-Cyclohexyl-2-{(S)-2-[5-(4-fluoro-phenoxy)-pyridin-3-yl}-pyrrolidin-1-yl}-2-oxo-ethyl)-2-methylamino-propionamide The title compound, hereinafter Compound C, can be prepared by the following reaction:

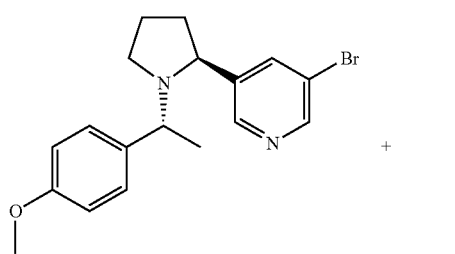
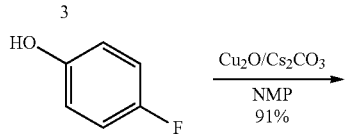
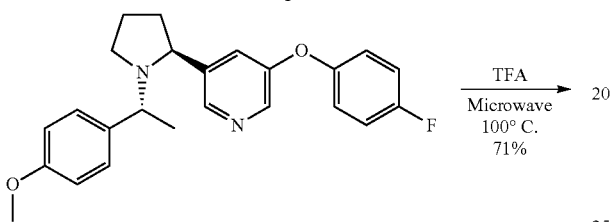
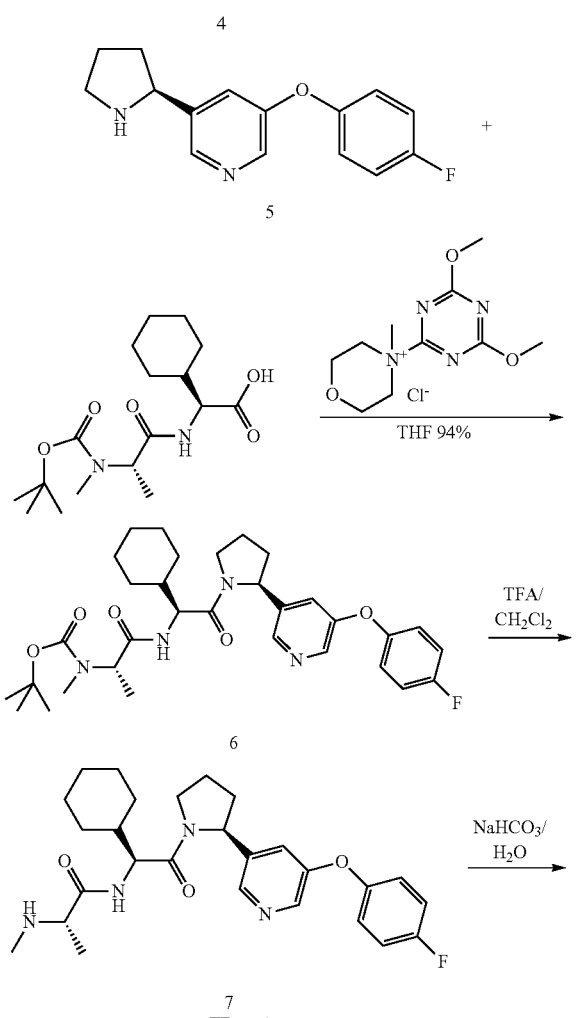

Step 1: 3-(4-Fluoro-phenoxy)-5-{(S)-1-[(R)-1-(4-methoxy-phenyl)-ethyl]-pyrrolidin-2-yl}-pyridine (4)

The mixture of 3-bromo-5-{(S)-1-[(R)-1-(4-methoxy-phenyl)-ethyl]-pyrrolidin-2-yl}-pyridine (3) (2.0 g, 5.54 mmole), 4-fluorophenol (3.1 g, 27.7 mmole), copper oxide (0.5 g, catalyst) and cesium carbonate (5.4 g, 16.6 mmole) in 10 mL of 1-N-methyl-2-pyrrolidinone is heated to 190° C. in a microwave reactor for 30 minutes. The reaction solution is diluted with 150 mL of EtOAc and filtered through celite. The filtrate is washed with 4×30 mL of water. The organic layer is concentrated and purified by flash column chromatography (hexane 100% to hexane 60% and EtOAc 40% by gradient in 20 minutes)) to give 3-(4-fluoro-phenoxy)-5-{(S)-1-[(R)-1-(4-methoxy-phenyl)-ethyl]-pyrrolidin-2-yl}-pyridine (4) (1.98 g, yield 91%) as a light yellow viscose liquid.

Step 2: 3-(4-Fluoro-phenoxy)-5-(S)-pyrrolidin-2-yl-pyridine (5)

A solution of 3-(4-fluoro-phenoxy)-5-{(S)-1-[(R)-1-(4-methoxy-phenyl)-ethyl]-pyrrolidin-2-yl}-pyridine (4) (1.98 g, 5.05 mmole) in 5 mL of TFA is heated at 100° C. in a microwave reactor for 20 minutes. The result solution is concentrated to remove TFA. The residue is diluted with 20 mL of $CH_2Cl_2$, and basified by washing with 5 mL of saturated sodium bicarbonate. The organic layer is concentrated and purified by flash column chromatography ($CH_2Cl_2$ 100% to $CH_2Cl_2$ 95% MeOH 5%) to give 3-(4-fluoro-phenoxy)-5-(S)-pyrrolidin-2-yl-pyridine (5) (923 mg, yield 71%) as pale yellow solid.

For the rest of the synthesis of Compound C, MS ESI 483.27 $(M+H)^+$, follow the corresponding procedures used in Example 2.

Example 4

(S)—N—((S)-1-Cyclohexyl-2-{(S)-2-[4-(4-fluoro-phenoxy)-pyridin-2-yl]-pyrrolidin-1-yl}-2-oxo-ethyl)-2-methylamino-propionamide The title compound, hereinafter Compound D, can be prepared by the following reaction scheme:

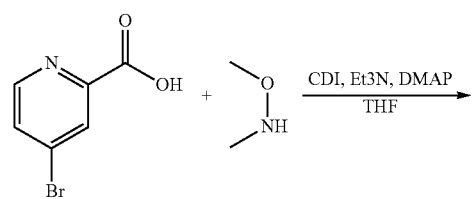
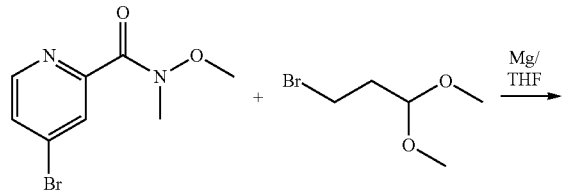
1
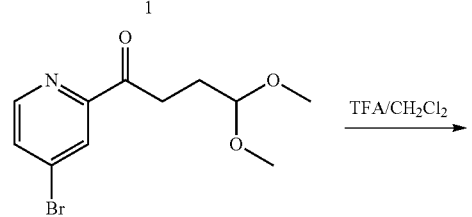
2
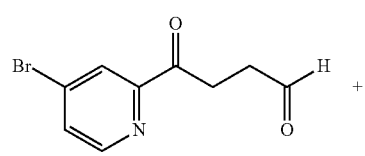
3
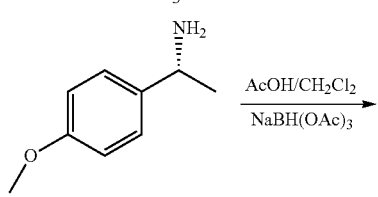
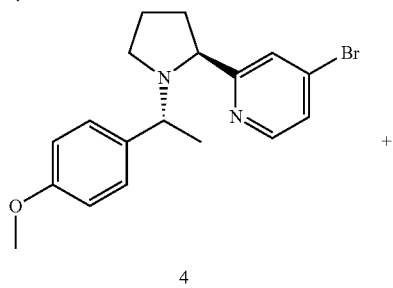
4
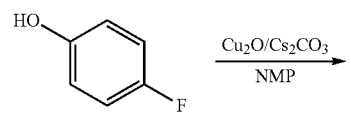
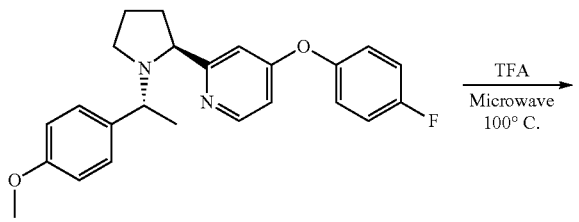
5
-continued
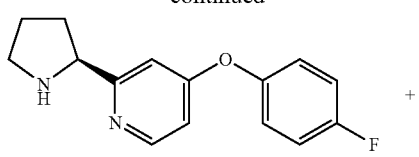
6
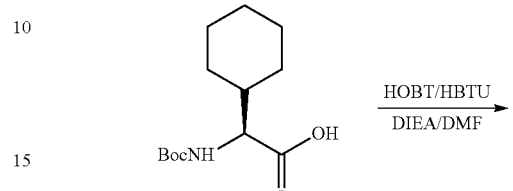
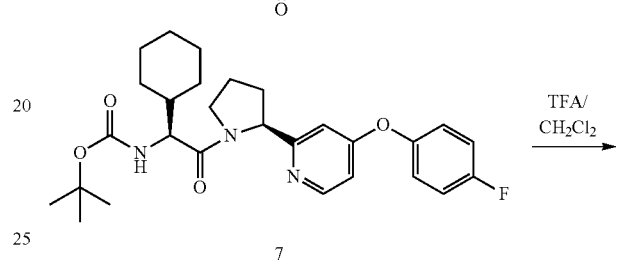
7
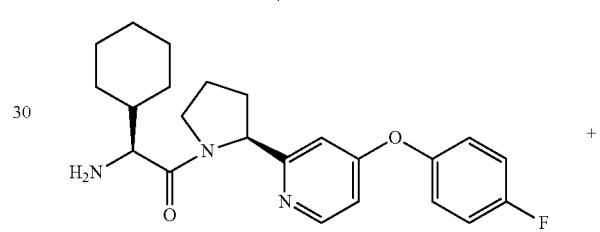
8
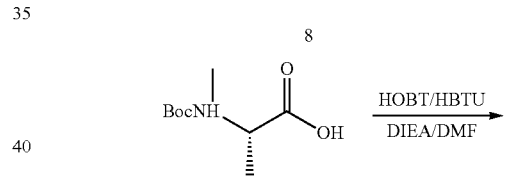
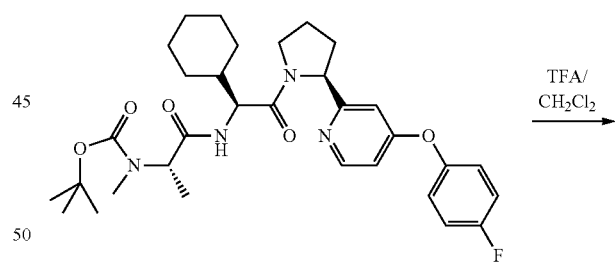
9
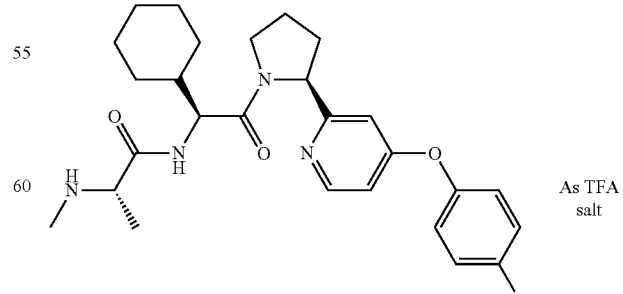
Compound D

Step 1: 4-Bromo-pyridine-2-carboxylic acid methoxy-methyl-amide (1)

To a solution of commercially-available 4-bromopicolinic acid (10.0 g, 49.5 mmole) in 200 mL of anhydrous THF at room temperature is added N,O-hydroxylamine hydrochloride (4.83 g, 49.5 mmol), triethylamine (6.9 mL, 49.5 mmol), carbonyl diimidazole (CDI) (12.0 g, 74.3 mmol) and N,N-dimethyl amino pyridine (DMAP) (20 mg, 0.16 mmol). After stirring at room temperature for 4 hours, an aliquot is taken and injected on LC-MS to check the reaction progress. Upon completion of the reaction, the reaction mixture is quenched with 100 mL of water and extracted with 2×150 mL of ethyl acetate. The combined organic layers are concentrated and purified by chromatography (hexanes 95%, EtOAc 5% step gradient) to give 4-bromo-pyridine-2-carboxylic acid methoxy-methyl-amide (1) as a thick yellow oil (10.4 g, yield 86%) MS ES+ 247.02.

Step 2: 1-(4-Bromo-pyridin-2-yl)-4,4-dimethoxy-butan-1-one (2)

To a solution of (1) (8.86 g, 36.2 mmole) in 250 mL of anhydrous THF in a 3-neck flamed dried round bottom flask at −70° C. (acetone-dry ice bath) is slowly added the Grignard reagent prepared from bromopropionaldehyde dimethyl acetal (16.5 g, 90.4 mmol) and Mg turnings (4.39 g, 181 mmol) in anhydrous THF (250 mL), maintaining internal temperature around −68° C. to −70° C. After stirring at −70° C. for 2 hours, the reaction mixture is diluted with 200 mL of water with the dry ice bath removed. The mixture is poured into a separatory funnel, and the mixture is extracted 3 times with ethyl acetate (150 mL). The organic layers are combined and dried over $Na_2SO_4$ and the solvent evaporated leaving a thick yellow oil (11 g, 100% crude yield, MS ES+258.02).

Step 3: 4-(4-Bromo-pyridin-2-yl)-4-oxo-butyraldehyde (3)

To a solution of 1-(4-bromo-pyridin-2-yl)-4,4-dimethoxy-butan-1-one (2) (crude from Step 2, 11 g, 38.2 mmol) in 100 of $CH_2Cl_2$ at room temperature is added trifluoroacetic acid (10.9 g, 95.4 mmol) and the reaction mixture is stirred overnight. The reaction is concentrated, the residue dissolved in ethyl acetate (150 mL) and washed with water 3 times. The organic layers are combined, dried over $Na_2SO_4$ and the solvent evaporated. The residue is purified by flash column chromatography (30% EtOAc in hexanes) to give 4-(4-bromo-pyridin-2-yl)-4-oxo-butyraldehyde (3) as an yellow oil. (4.16 g, 45%): MS ES+244.04.

Step 4: 4-Bromo-2-{(1S,2S)-1-[1-(4-methoxy-phenyl)-ethyl]-pyrrolidin-2-yl}-pyridine (4)

To a solution of 4-(4-bromo-pyridin-2-yl)-4-oxo-butyraldehyde (3) (720 mg, 2.97 mmol) in $CH_2Cl_2$ at −70° C. is added acetic acid (8.93 mg, 0.15 mmol), $NaBH(OAc)_3$ (1.58 g, 7.44 mmol) and (R)-(+)-1-(4-methoxyphenyl)ethylamine (540 mg, 3.6 mmol). The reaction mixture is stirred at −70° C. for 1 hour, then warmed up to room temperature by removing the ice bath and letting it stir for another 2 hours. The reaction mixture is quenched by adding water (25 mL) is washed with 4×20 mL of water. The combined organic layers is concentrated and purified by flash column chromatography (hexane 70%, EtOAc 30%) to yield 4-bromo-2-{(1S,2S)-1-[1-(4-methoxy-phenyl)-ethyl]-pyrrolidin-2-yl}-pyridine (4) (386 mg, 36% yield) as a yellow solid: MS ES+363.10.

For the rest of the synthesis of Compound D, MS ESI 483.27 (M+H)+, follow the corresponding procedures used in the synthesis of Examples 1 and 3.

Example 5

(S)—N-[(S)-Cyclohexyl-2-((S)-2-{5-fluoro-2-[(4-fluoro-phenyl)-methyl-amino]-pyridin-4-yl}-pyrrolidin-1-yl)-2-oxo-ethyl]-2-methylamino-propionamide The title compound, herein after, Compound E, is prepared by the following reaction scheme:

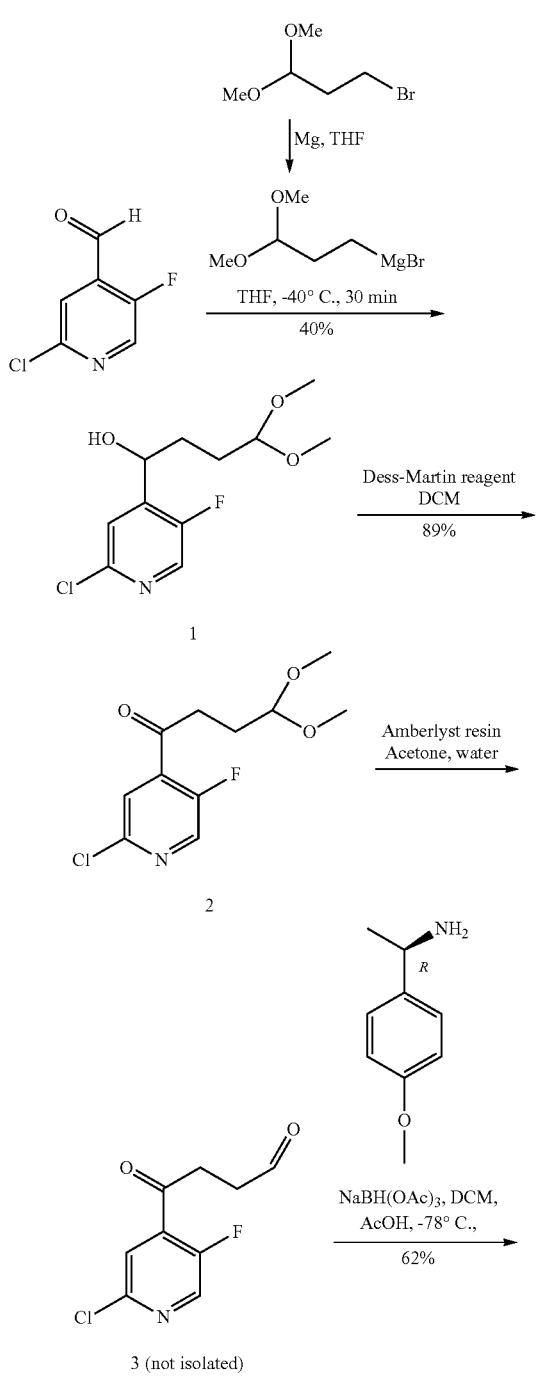

-continued

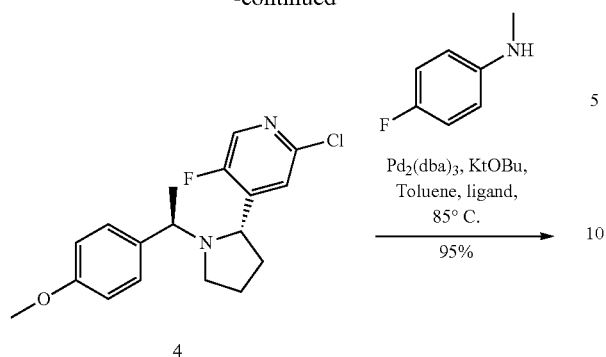

4

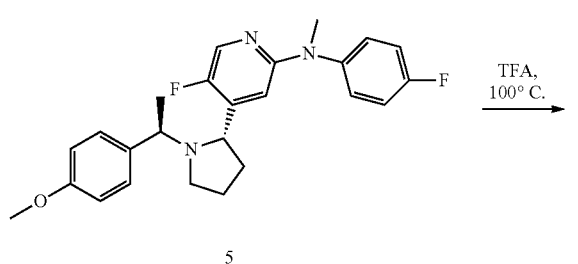

5

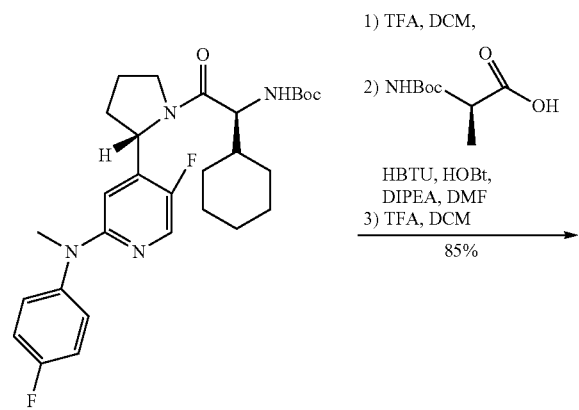

6 (not isolated)

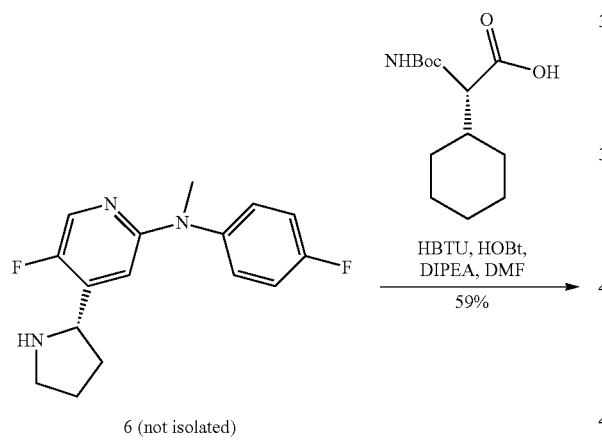

7

-continued

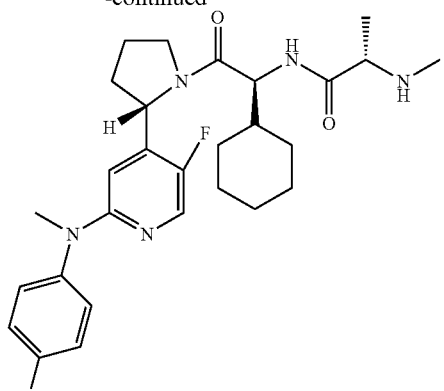

Compound E

1-(2-Chloro-5-fluoro-pyridin-4-yl)-4,4-dimethoxy-butan-1-ol (1)

To a solution of Mg (0.71 g, 30 mmol) in THF (10 mL) are added cat. iodine and a solution of 3-bromo-1,1-dimethoxy-propane (3.99 g, 21.57 mmol) in THF (10 mL). The mixture is stirred at room temperature for 2 hours. At −30° C., to a solution of 2-chloro-5-fluoro-pyridine-4-carbaldehyde (2.0 g, 12.54 mmol) in THF (5 mL) is added to the above prepared Grignard reagent. The mixture is stirred at this temperature for 2 hours. Then the reaction mixture is cooled in an ice bath, saturated NH$_4$Cl and water are added and the mixture is extracted with EtOAc. The combined organic layers are washed with brine, dried over Na$_2$SO$_4$, filtered and concentrated down. The crude product is purified by chromatography (EtOAc/hexane: 10%~40%) to give 1-(2-chloro-5-fluoro-pyridin-4-yl)-4,4-dimethoxy-butan-1-ol (0.81 g, 25%). M/Z=264.13[M+1]

1-(2-Chloro-5-fluoro-pyridin-4-yl)-4,4-dimethoxy-butan-1-one (2)

The suspension of 1-(2-chloro-5-fluoro-pyridin-4-yl)-4,4-dimethoxy-butan-1-ol (0.80 g, 3.03 mmol) and Dess-Martin reagent (1.54 g, 3.64 mmol) in DCM (20 mL) is stirred at room temperature for 3 hours. The precipitate is filtered. Water is added to the filtrate and extracted with DCM. The combined organic layers are washed with water, brine, dried over Na$_2$SO$_4$, filtered and concentrated down. The crude product is purified by chromatography (EtOAc/hexane: 5%~20%) to give 1-(2-chloro-5-fluoro-pyridin-4-yl)-4,4-dimethoxy-butan-1-one (0.71 g, 89%). M/Z=262.10 [M+1]

1-(2-Chloro-5-fluoro-4-{(S)-1-[(R)-1-(4-methoxy-phenyl)-ethyl]-pyrrolidin-2-yl}-pyridine (4)

To a solution of 1-(2-chloro-5-fluoro-pyridin-4-yl)-4,4-dimethoxy-butan-1-one (0.71 g, 2.71 mmol) in acetone (15 mL) is added Amberlyst resin 15 (1.1 g) and water (0.5 mL). After mechanical shaking for 3 hours at room temperature, the mixture is filtered. The resin beads are washed with acetone and dichloromethane. The filtrate is concentrated down to give 4-(2-chloro-5-fluoro-pyridin-4-yl)-4-oxo-buty-laldehyde (3), which is used in next step without further purification.

The solution of 4-(2-chloro-5-fluoro-pyridin-4-yl)-4-oxo-butylaldehyde in dichloromethane (25 mL) is cooled to −78° C., then sodium triethoxyborohydride (1.72 g, 8.14 mmol) and acetic acid (0.2 mL) are added. After the mixture was stirred at this temperature for 30 minutes, R(+)-α-methylbenzylamine (0.39 g, 2.57 mmol) is added and the mixture was warmed up to room temperature overnight. Saturated NaHCO$_3$ is added to the mixture and the layers are separated. The aqueous layer is extracted with dichloromethane and the combined organic layers are washed with brine, dried over Na$_2$SO$_4$, filtered and concentrated down. The crude product is purified by chromatography (EtOAc/hexane: 5%~20%) to give 1-(2-chloro-5-fluoro-4-{(S)-1-[(R)-1-(4-methoxy-phenyl)-ethyl]-pyrrolidin-2-yl}-pyridine (0.57 g, 62%). HR Mass M/Z=335.1330 [M+1]

(5-Fluoro-4-{(S)-1-[(R)-1-(4-methoxy-phenyl)-ethyl]-pyrrolidin-2-yl}-pyridin-2-yl)-(4-fluoro-phenyl)-methyl-amine (5)

To a solution of 1-(2-chloro-5-fluoro-4-{(S)-1-[(R)-1-(4-methoxy-phenyl)-ethyl]-pyrrolidin-2-yl}-pyridine (100 mg, 0.30 mmol) in toluene (25 mL) are added (4-fluoro-phenyl)-methyl-amine (48 mg, 0.39 mmol), 2-(dicyclohexylphosphino)-biphenyl (10 mg, 0.03 mmol), Pd$_2$(dba)$_3$ (14 mg, 0.015 mmol) and potassium tert-butoxide (84 mg, 0.75 mmol). The reaction mixture is stirred at 85° C. for 3 hours and cooled to room temperature. Water and EtOAc are added to the mixture. The layers are separated and the aqueous layer is extracted with EtOAc. The combined organic layers are washed with brine, dried over Na$_2$SO$_4$, filtered and concentrated down. The crude product is purified by chromatography (EtOAc/hexane: 10%~40%) to give (5-fluoro-4-{(S)-[(R)-1-(4-methoxy-phenyl)-ethyl]-pyrrolidin-2-yl}-pyridin-2-yl)-(4-fluoro-phenyl)-methyl-amine (120 mg, 95%). M/Z=424.23 [M+1]

For the rest of the synthesis of Compound E, MS ESI 514.30 (M+H)$^+$, follow the corresponding procedures used in the synthesis of Examples 1 and 3.

Examples 6-31

The following compounds are made by procedures similar to those in the above examples.

| Ex. | Name | +MS ESI (M + H)$^+$ |
|---|---|---|
| 6 | (S)-N-((S)-1-Cyclohexyl-2-{(S)-2-[4-(4-fluoro-benzoyl)-5-methyl-thiazo-l-2-yl]-pyrrolidin-1-yl}-2-oxo-ethy-l)-2-methylamino-propionamide | 515 |
| 7 | (S)-N-{(S)-2-[(S)-2-(4-Benzoyl-5-methyl-oxazol-2-yl)-pyrrolidin-1-yl]-1-cyclohexyl-2-oxo-ethyl}-2-methylamino-propionamide | 481 |
| 8 | (S)-N-((S)-1-Cyclohexyl-2-{(S)-2-[4-(4-fluoro-benzoyl)-5-methyl-oxazol-2-yl]-pyrrolidin-1-yl}-2-oxo-ethyl)-2-methylamino-propionamide | 499 |
| 9 | (S)-N-((S)-1-Cyclohexyl-2-{(S)-2-[4-(4-fluoro-benzoyl)-5-methyl-thiazol-2-yl]-pyrrolidin-1-yl}-2-oxo-ethyl)-2-methylamino-propionamide | 487 |
| 10 | (S)-N-{(S)-2-[(S)-2-(4-Benzoyl-oxazol-2-yl)-pyrrolidin-1-yl]-1-cyclohexyl-2-oxo-ethyl}-2-methylamino-propionamide | 485 |
| 11 | (S)-N-((S)-1-Cyclohexyl-2-{(S)-2-[4-(2,4-difluoro-benzoyl)-thiazol-2-yl]-pyrrolidin-1-yl}-2-oxo-ethyl)-2-methylamino-propionamide | 519 |
| 12 | (S)-N-((S)-1-Cyclohexyl-2-{(S)-2-[4-(1H-indole-2-carbonyl)-thiazol-2-yl]-pyrrolidin-1-yl}-2-oxo-ethyl)-2-methylamino-propionamide | 522 |
| 13 | (S)-N-((S)-1-Cyclohexyl-2-{(S)-2-[2-(4-fluoro-phenoxy)-pyridin-4-yl]-pyrrolidin-1-yl}-2-oxo-ethyl)-2-methylamino-propionamide | 483.27 |
| 14 | (S)-N-[(S)-1-((S)-2-{2-[(4-Fluoro-phenyl)-methyl-amino]-pyridin-4-yl}-pyrrolidine-1-carbonyl)-2-methyl-propyl]-2-methylamino-propionamide | 456.27 |
| 15 | (S)-N-((S)-1-Cyclohexyl-2-{(S)-2-[2-(4-fluoro-benzoyl)-pyridin-4-yl]-pyrrolidin-1-yl}-2-oxo-ethyl)-2-methylamino-propionamide | 495.27 |
| 16 | (S)-N-((S)-1-Cyclohexyl-2-{(S)-2-[2-(5-fluoro-pyridin-2-ylamino)-pyridin-4-yl]-pyrrolidin-1-yl}-2-oxo-ethyl)-2-methylamino-propionamide | 483.28 |
| 17 | (S)-N-[(S)-1-Cyclohexyl-2-((S)-2-{3-fluoro-2-[(4-fluoro-phenyl)-methyl-amino]-pyridin-4-yl}-pyrrolidin-1-yl)-2-oxo-ethyl]-2-methylamino-propionamide | 514.29 |
| 18 | (S)-N-((S)-1-Cyclohexyl-2-{(S)-2-[3-fluoro-2-(4-fluoro-benzoyl)-pyridin-4-yl]-pyrrolidin-1-yl}-2-oxo-ethyl)-2-methylamino-propionamide | 513.26 |
| 19 | (S)-N-[(S)-2-((S)-2-{2-Amino-6-[N-(4-fluoro-phenyl)-hydrazino]-pyridin-4-yl}-pyrrolidin-1-yl)-1-cyclohexyl-2-oxo-ethyl]-2-methylamino-propionamide | 512.31 |
| 20 | (S)-N-{(S)-1-Cyclohexyl-2-oxo-2-[(S)-2-(4-phenoxy-pyridin-2-yl)-pyrrolidin-1-yl]-ethyl}-2-methylamino-propionamide | 465.3 |
| 21 | (S)-N-((S)-1-Cyclohexyl-2-{(S)-2-[6-(4-fluoro-phenoxy)-2-methyl-pyrimidin-4-yl]-pyrrolidin-1-yl}-2-oxo-ethyl)-2-methylamino-propionamide | 498.3 |
| 22 | (S)-N-((S)-1-Cyclohexyl-2-{(S)-2-[4-(4-fluoro-benzoyl)-pyridin-2-yl]-pyrrolidin-1-yl}-2-oxo-ethyl)-2-methylamino-propionamide | 495.3 |
| 23 | (S)-N-((S)-1-Cyclohexyl-2-{(S)-2-[6-(4-fluoro-benzoyl)-2-methyl-pyrimidin-4-yl]-pyrrolidin-1-yl}-2-oxo-ethyl)-2-methylamino-propionamide | 510.3 |
| 24 | (S)-N-[(S)-1-Cyclohexyl-2-((S)-2-{5-[(4-fluoro-phenyl)-methyl-amino]-pyridin-3-yl}-pyrrolidin-1-yl)-2-oxo-ethyl]-2-methylamino-propionamide | 496.3 |

-continued

| Ex. | Name | +MS ESI (M + H)+ |
|---|---|---|
| 25 | (S)-N-[(S)-1-Cyclohexyl-2-((S)-2-{4-[(4-fluoro-phenyl)-methyl-amino]-pyridin-2-yl}-pyrrolidin-1-yl)-2-oxo-ethyl]-2-methylamino-propionamide | 496.3 |
| 26 | (S)-N-[(S)-1-Cyclohexyl-2-((S)-2-{6-[(4-fluoro-phenyl)-methyl-amino]-2-methyl-pyrimidin-4-yl}-pyrrolidin-1-yl)-2-oxo-ethyl]-2-methylamino-propionamide | 511.3 |
| 27 | (S)-N-((S)-1-{(S)-2-[6-(4-Fluoro-benzoyl)-2-methyl-pyrimidin-4-yl]-pyrrolidine-1-carbonyl}-2-methyl-propyl)-2-methylamino-propionamide | 458.2 |
| 28 | (S)-N-((S)-1-{(S)-2-[6-(4-Fluoro-benzoyl)-2-methyl-pyrimidin-4-yl]-pyrrolidine-1-carbonyl}-2-methyl-propyl)-2-methylamino-propionamide | 470.2 |
| 29 | (S)-N-[(S)-1-((S)-2-{6-[(4-Fluoro-phenyl)-methyl-amino]-2-methyl-pyrimidin-4-yl}-pyrrolidine-1-carbonyl)-2-methyl-propyl]-2-methylamino-propionamide | 471.3 |
| 30 | (S)-N-((S)-1-Cyclohexyl-2-{(S)-2-[6-(4-fluoro-phenylamino)-2-methyl-pyrimidin-4-yl]-pyrrolidin-1-yl}-2-oxo-ethyl)-2-methylamino-propionamide | 497.3 |
| 31 | (S)-N-((S)-1-{(S)-2-[6-(4-Fluoro-phenylamino)-2-methyl-pyrimidin-4-yl]-pyrrolidine-1-carbonyl}-2-methyl-propyl)-2-methylamino-propionamide | 457.3 |

In order to measure the ability of the inventive compounds to bind the BIR3 peptide binding pocket an ELISA and a cell based assays are utilized.

Example 32

Elisa

Compounds are incubated with GST-BIR3 fusion protein and biotinylated SMAC peptide (AVPFAQK) in stretavidin-coated 96-well plates. For XIAP BIR3 Smac Elisa, a GST-BIR3 fusion containing amino acids 248-358 from XIAP is used. For CIAP1 BIR3 Smac Elisa, a GST-BIR3 fusion containing amino acids 259-364 from CIAP1 is used. Following a 30-minute incubation, wells are extensively washed. The remaining GST-BIR3 fusion protein is monitored by ELISA assay involving first, incubation with goat anti-GST antibodies followed by washing and incubation with alkaline phosphatase conjugated anti-goat antibodies. Signal is amplified using Attophos (Promega) and read with Cytoflour Ex 450 nm/40 and Em 580 nm. $IC_{50}$s correspond to concentration of compound which displaces half of GST-BIR3 signal. The $IC_{50}$ for non-biotinylated Smac is 400 nM. The $IC_{50}$ values of compounds of Examples 1-4 in the described ELISA assays ranged from <0.001-10 µM.

Example 33

Cell Proliferation Assay

The ability of compounds to inhibit tumor cell growth in vitro is monitored using the CellTiter 96® AQ$_{ueous}$ Non-Radioactive Cell Proliferation Assay (Promega). This assay is composed of solutions of a novel tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS. MTS is bioreduced by cells into a formazan product, the absorbance of which is measured at 490 nm. The conversion of MTS into the aqueous soluble formazan product is accomplished by dehydrogenase enzymes found in metabolically active cells. The quantity of formazan product as measured by the amount of 490 nm absorbance is directly proportional to the number of living cells in culture. The $IC_{50}$ values of compounds described in Examples 1-4 in this cell assay ranged from <0.001-50 µM.

Example 34

Tablets 1 Comprising Compounds of the Formula (I)

Tablets, comprising, as active ingredient, 50 mg of any one of the compounds of formula (I) mentioned in the preceding Examples 1-4 of the following composition are prepared using routine method:

| Composition | |
|---|---|
| Active Ingredient | 50 mg |
| Wheat starch | 60 mg |
| Lactose | 50 mg |
| Colloidal silica | 5 mg |
| Talcum | 9 mg |
| Magnesium stearate | 1 mg |
| Total | 175 mg |

Manufacture:

The active ingredient is combined with part of the wheat starch, the lactose and the colloidal silica and the mixture pressed through a sieve. A further part of the wheat starch is mixed with 5-fold amount of water on a water bath to form a paste and the mixture made first is kneaded with this paste until a weakly plastic mass is formed.

The dry granules are pressed through a sieve having a mesh size of 3 mm, mixed with a pre-sieved mixture (1 mm sieve) of the remaining corn starch, magnesium stearate and talcum and compressed to form slightly biconvex tablets.

Example 35

Tablets 2 Comprising Compounds of the Formula (I)

Tablets, comprising, as active ingredient, 100 mg of any one of the compounds of formula (I) of Examples 1-4 are prepared with the following standard procedures:

| Composition | |
|---|---|
| Active Ingredient | 100 mg |
| Crystalline lactose | 240 mg |
| Avicel | 80 mg |
| PVPPXL | 20 mg |
| Aerosil | 2 mg |
| Magnesium stearate | 5 mg |
| Total | 447 mg |

Manufacture:

The active ingredient is mixed with the carrier materials and compressed by means of a tabletting machine (Korsch EKO, Stempeldurchmesser 10 mm).

Example 36

Capsules

Capsules, comprising as active ingredient, 100 mg of any one of the compounds of formula (I) given in Examples 1-4, of the following composition are prepared according to standard procedures:

| Composition | |
|---|---|
| Active Ingredient | 100 mg |
| Avicel | 200 mg |
| PVPPXL | 15 mg |
| Aerosil | 2 mg |
| Magnesium stearate | 1.5 mg |
| Total | 318.5 mg |

Manufacturing is done by mixing the components and filling them into hard gelatine capsules, size 1.

The term "active ingredient", as used herein, refers to a compound of formulae (I)-(VII) or a pharmaceutically acceptable salt thereof, as defined herein.

The above preferred embodiments are given to illustrate the scope and spirit of the present invention. The descriptions provided herein will make apparent to those skilled in the art other embodiments and examples. These other embodiments and examples are within the contemplation of the present invention. Therefore, the present invention should be limited only by the appended claims.

What is claimed is:

1. A compound of Formula 5

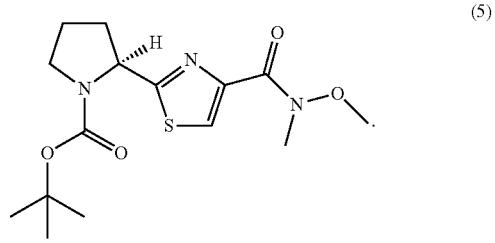 [SMILES: CON(C)C(=O)c1csc([C@@H]2CCCN2C(=O)OC(C)(C)C)n1]

(5)

2. A compound of Formula 6

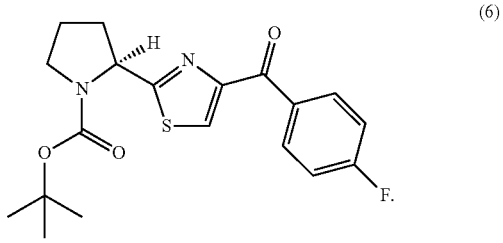 [SMILES: CC(C)(C)OC(=O)N1CCC[C@H]1c1nc(C(=O)c2ccc(F)cc2)cs1]

(6)

3. A compound of Formula 7

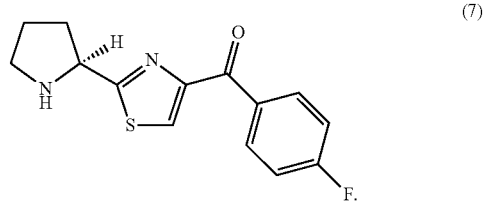 [SMILES: O=C(c1ccc(F)cc1)c1csc([C@@H]2CCCN2)n1]

(7)

* * * * *